US011343910B2

(12) United States Patent
Chung et al.

(10) Patent No.: US 11,343,910 B2
(45) Date of Patent: May 24, 2022

(54) ELASTIC PRINTED CONDUCTORS

(71) Applicant: THE GOVERNORS OF THE UNIVERSITY OF ALBERTA, Edmonton (CA)

(72) Inventors: Hyun-Joong Chung, Edmonton (CA); Jana Rieger, Edmonton (CA); Thanh-Giang La, Edmonton (CA); Shide Qiu, Edmonton (CA); Dylan Scott, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 0 days.

(21) Appl. No.: 17/059,293

(22) PCT Filed: Jun. 7, 2019

(86) PCT No.: PCT/IB2019/054782
§ 371 (c)(1),
(2) Date: Nov. 27, 2020

(87) PCT Pub. No.: WO2019/237711
PCT Pub. Date: Dec. 12, 2019

(65) Prior Publication Data
US 2021/0144848 A1  May 13, 2021

Related U.S. Application Data

(60) Provisional application No. 62/682,022, filed on Jun. 7, 2018.

(51) Int. Cl.
*H05K 1/02* (2006.01)
*H05K 3/12* (2006.01)
(Continued)

(52) U.S. Cl.
CPC ....... *H05K 1/0283* (2013.01); *A61B 5/02055* (2013.01); *A61B 5/296* (2021.01);
(Continued)

(58) Field of Classification Search
CPC .......... H05K 1/095; H05K 1/038; H05K 1/11; H05K 1/0283; H05K 3/125; H05K 3/12; H05K 3/32; A61B 5/0245
See application file for complete search history.

(56) References Cited

U.S. PATENT DOCUMENTS

2009/0282671 A1   11/2009  Tao et al.

FOREIGN PATENT DOCUMENTS

| JP | 2011529121 A  | 12/2011 |
| WO | 2017197228 A2 | 11/2017 |
| WO | 2017199594 A1 | 11/2017 |

OTHER PUBLICATIONS

Canadian Intellectual Property Office (CIPO), International Search Report and Written Opinion for PCT/IB2019/054782, dated Oct. 1, 2019.

(Continued)

*Primary Examiner* — Jeremy C Norris
(74) *Attorney, Agent, or Firm* — Norton Rose Fulbright Canada LLP

(57) ABSTRACT

The development of stretchable, mechanically and electrically robust interconnects by printing an elastic, silver-based composite ink onto stretchable fabric. Such interconnects can have conductivity of 3000-4000 S/cm and are durable under cyclic stretching. In serpentine shape, the fabric-based conductor is enhanced in electrical durability. Resistance increases only ~5 times when cyclically stretched over a thousand times from zero to 30% strain at a rate of 4% strain per second due to the ink permeating the textile structure. The textile fibers are wetted with composite ink to form a (Continued)

conductive, stretchable cladding of the silver particles. The e-textile can realize a fully printed, double-sided electronic system of sensor-textile-interconnect integration. The double-sided e-textile can be used for a surface electromyography (sEMG) system to monitor muscles activities, an electroencephalography (EEG) system to record brain waves, and the like.

24 Claims, 20 Drawing Sheets

(51) Int. Cl.
| | | |
|---|---|---|
| A61B 5/02 | (2006.01) | |
| A61B 5/296 | (2021.01) | |
| A61B 5/0205 | (2006.01) | |
| A61B 5/00 | (2006.01) | |
| C09D 11/10 | (2014.01) | |
| H05K 1/09 | (2006.01) | |
| A61B 5/291 | (2021.01) | |
| A61B 5/297 | (2021.01) | |
| A61B 5/28 | (2021.01) | |
| A61B 5/0245 | (2006.01) | |
| A61B 5/08 | (2006.01) | |
| C08K 3/08 | (2006.01) | |
| H05K 1/03 | (2006.01) | |

(52) U.S. Cl.
CPC ............ *A61B 5/6804* (2013.01); *C09D 11/10* (2013.01); *H05K 1/095* (2013.01); *H05K 3/125* (2013.01); *A61B 5/0245* (2013.01); *A61B 5/0816* (2013.01); *A61B 5/28* (2021.01); *A61B 5/291* (2021.01); *A61B 5/297* (2021.01); *A61B 2562/0209* (2013.01); *A61B 2562/0247* (2013.01); *A61B 2562/0261* (2013.01); *A61B 2562/164* (2013.01); *A61B 2562/166* (2013.01); *C08K 3/08* (2013.01); *C08K 2003/0806* (2013.01); *H05K 1/038* (2013.01); *H05K 2201/0116* (2013.01); *H05K 2201/0215* (2013.01); *H05K 2201/0245* (2013.01); *H05K 2201/0278* (2013.01); *H05K 2201/09263* (2013.01); *H05K 2203/1545* (2013.01); *H05K 2203/1572* (2013.01)

(56) References Cited

OTHER PUBLICATIONS

European Patent Office, Partial Supplementary European Search Report against EP Application No. 19815511.1, dated Dec. 23, 2021.

Nanocomposite ink        Commercial ink

Printing Process of Double-side E-textiles

ELASTIC PRINTED CONDUCTORS

RELATED APPLICATIONS

This application claims priority under 35 U.S.C. § 119(e) to U.S. Provisional Patent Application No. 62/682,022 filed Jun. 7, 2018, which is incorporated herein by reference.

BACKGROUND OF THE INVENTION

Wearable health care electronics are developed to ultimately integrate with daily textiles and clothes, so that the wearable electronics can be featured with the fabrics' unique characteristics of skin comfort, softness, thermal dissipation, breathability, light weight, and high conformability (1,2,3). Fabric-based electronics, also known as known as 'e-textiles', are emerging as a next-generation class in which electronics are built on textile fibers (4,5,6,7,8,9). E-textiles are inspiring a number of research efforts for biomedical and health care assessment (1,10). In the vision of fully integrated e-textile systems, fundamental flexible electronics like semiconducting transistors (11,12), processing units (13,14), sensors (15,16,17,18,19,20), generators (21,22,23, 24,25), and energy storage units (26,27) would be developed toward integration onto or into textiles. In the last decade, the reported research efforts have employed several strategies for realizing smart e-textiles such as (i) integrating electronic units onto 2D fabric substrates (8,21,28), and (ii) interweaving 1D thread-like electrode devices into fabric structures (29). The latter strategy is limited in miniaturization and flexibility since the electronic threads, consisting of various functional layers, are prone to mechanical stiffening, un-conformability, and adverse interconnection between multi-thread and signal acquisition electronics. For such reasons, e-textiles with electronics embedded on 2D fabric substrates are strategically developed in a large spectrum of applications.

The recent breakthroughs in thin-film flexible devices have provided high-resolution biophysiological measurements such as electrical signals (30,31), electrochemical signals from sweat (32), temperature (33,34), tactile force (35), and blood glucose (36). E-textile systems can be realized by embedding these thin-film devices on textiles to take advantages of the high-performance electronics. To achieve a fully integrated e-textile, stretchable interconnects/wirings are central in order to stably connect the prefabricated thin devices and textiles. Several fabric-based wires have been used such as (i) knitting or weaving 1D conductive threads into textiles (37), (ii) fully coating 2D textile sheets with conductive materials (38), and (iii) stencil and screen printing conductive ink on textiles (39). In recent reported works (39,40), viscous composite inks were printed via a patterned stencil onto a textile sheet to form stretchable wires which are low in surface resistivity of 0.06 $\Omega sq^{-1}$. However, despite permeation of the composite ink into the textile by using certain solvents, the ink-textile wires still needed multiple-layered printing (5 overlays) and high-temperature (160° C.) pressing to be capable of cyclic stretching up to 1000 times with an increase of one-order in resistance (from zero to 10% strain). Such hot-press processing, however, would hasten thermal degradation of most of daily fabrics, with a significant decrease in performance when treated between the temperature range of 125° C.-180° C. (41).

SUMMARY

In this work, we develop a stretchable, mechanically and electrically robust e-textile that fully integrates sensors and interconnects by printing silver-based composite ink onto stretchable fabric (FIG. 1). The printed, textile-based conductors have high conductivity (3000-4000 S/cm), and are able to stretch more than 100% in uniaxial strain with one-order increase in resistance. Furthermore, when laid out in a serpentine shape, the textile-based interconnect demonstrates enhanced electrical durability as it only increases ~5 times in resistance when cyclically stretched over a thousand times from zero to 30% strain at a rate of 4% strain per second. Such enhancement is possible due to the 'wetting' of the textile fibers with composite ink to form a conductive, stretchable cladding of the silver particles along the fibers. We further use the textile-based conductors to manufacture monitoring systems for (i) surface electromyography (sEMG) sensing of human muscles activities, and (ii) electroencephalography (EEG) sensing of human brain waves. These textile-based biosensors adhered and conformed well to the skin for high quality biosensing applications.

Accordingly, this disclosure provides an electronic textile apparatus comprising:
a) a porous textile having fibers, a surface and an opposite surface;
b) a patterned electrically conductive wire that coats a portion of the fibers at the surface of the textile;
c) an electrode that coats a portion of the fibers at the opposite surface of the textile; and
d) an electrically conductive interconnect that coats a portion of the fibers within the textile, disposed between the surface and the opposite surface of the textile, and in contact with the wire and the electrode;
wherein the wire, the electrode and the interconnect comprise an elastomer and metal particles.

This disclosure also provides an ink composition comprising about 1 part to about 5 parts of a fluorocopolymer (a), about 1 part to about 5 parts of an organic solvent (b), and about 1 part to about 5 parts of metal flakes (c).

Additionally, this disclosure provides a method for fabricating a stretchable electronic textile from the ink composition above, comprising:
a) printing a circuit with the ink composition on a porous textile having fibers;
wherein a wire is printed on a surface of the textile, and an electrode is printed on the opposite surface of the textile;
b) inserting the ink composition into the textile to provide an electrical contact between the wire and the electrode, thereby forming a completed circuit;
c) drying the completed circuit;
wherein the printable ink coats a portion of the fibers that forms the completed circuit, and the textile has an electrical resistance ratio of about 10 or less than 10 after about 1000 cyclic stretches from zero to about 30% strain at a rate of about 4% strain per second.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
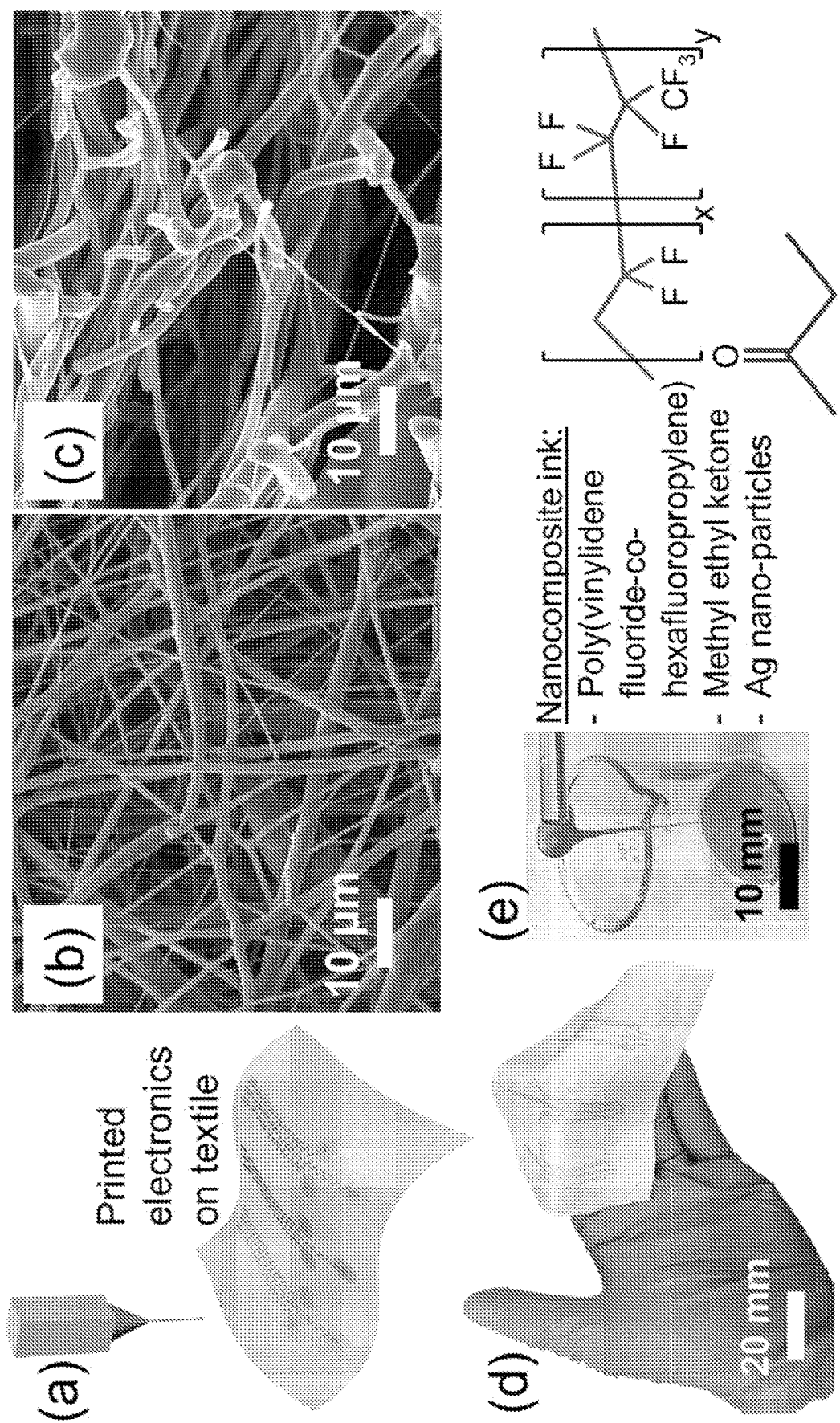
FIG. 1. Printed, stretchable fabric conductors.
Figure 1:
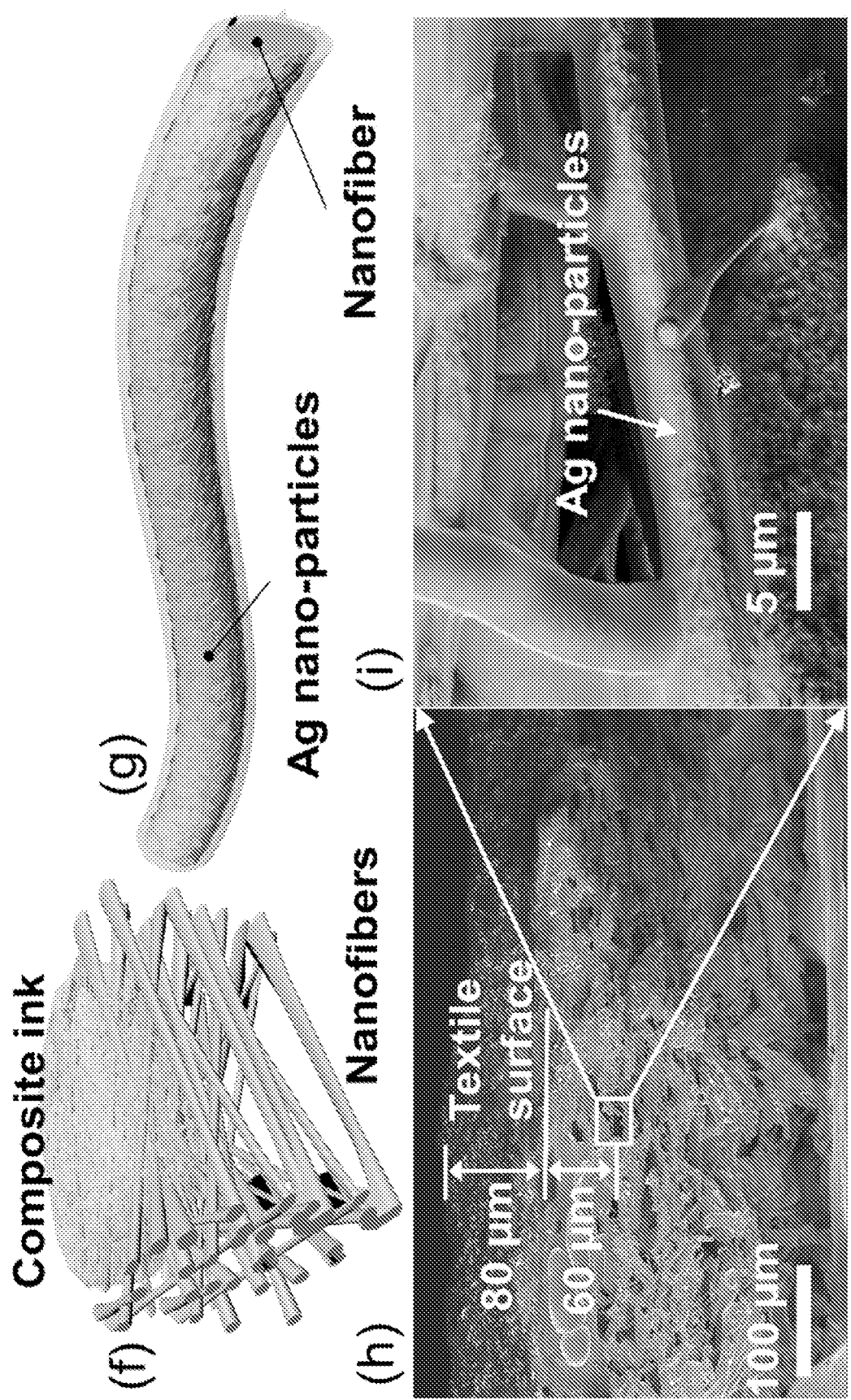
Figure 11:
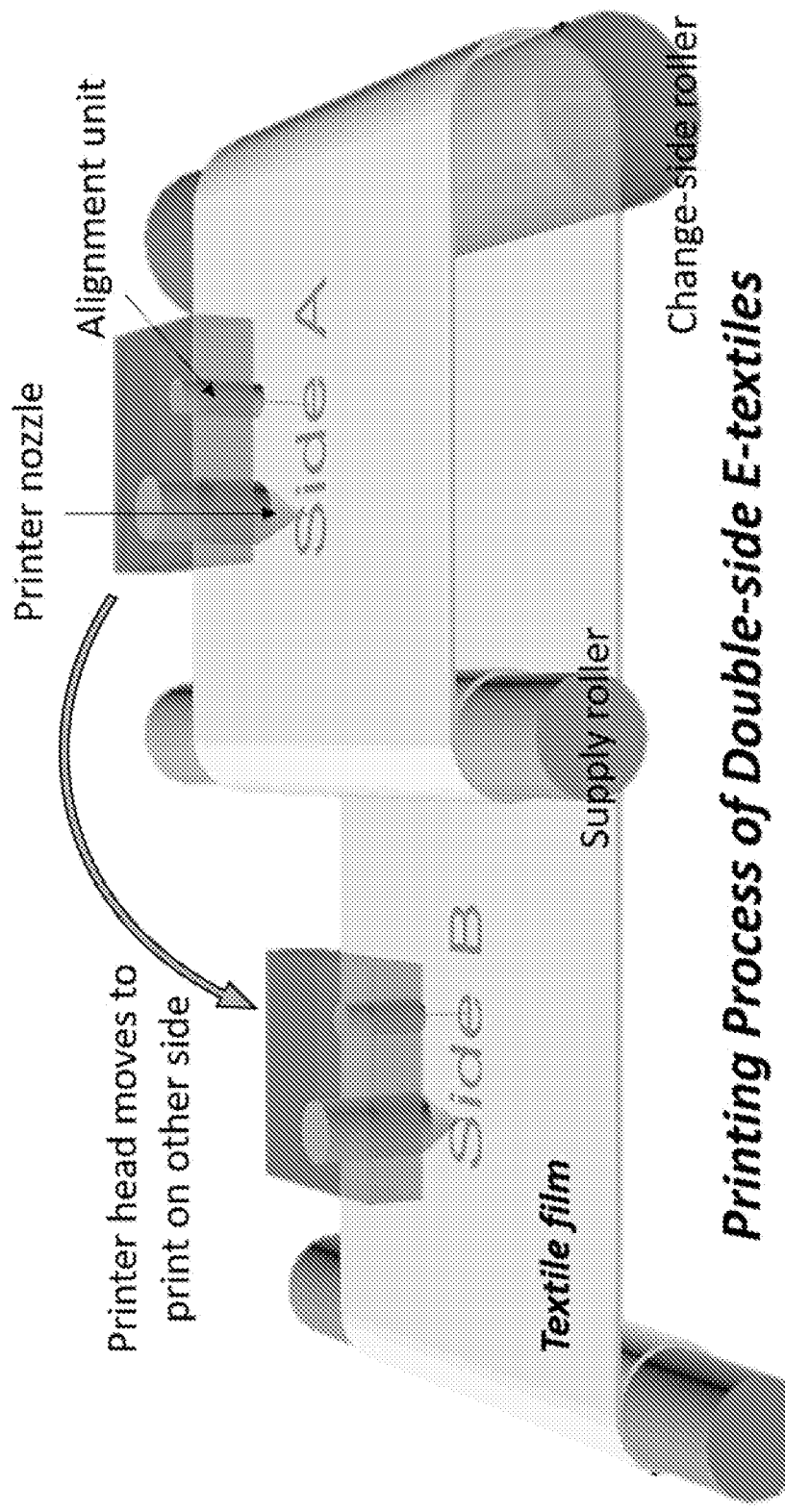
FIG. 11. One embodiment of one-step printing process.

Fabrication of our e-textile is simple and is manufactured in a one-step printing process without post-treatment (see FIG. 1(*a*), and FIG. 11). We printed a composite ink on a stretchable, nonwoven polyurethane (PU) fiber substrate. The full printed e-textile with interconnects and sensors is inherent of conformality, breathability, and flexibility (see FIG. 1(*b*)). The printing is a rapid process, and capable of mass-production. After one-step printing, the specimens are dried in room condition. Details of the manufacturing process are discussed below.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14*th* Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, or in a reaction mixture.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone, 2-butanone, and 3-pentanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone or two or more of them may be mixed for use to provide a "solvent system".

Embodiments of the Invention

This disclosure provides an electronic textile apparatus comprising:
a) a porous textile having fibers, a surface and an opposite surface;
b) a patterned (e.g., serpentine patterned) electrically conductive wire that coats a portion of the fibers at the surface of the textile;
c) an electrode that coats a portion of the fibers at the opposite surface of the textile; and
d) an electrically conductive interconnect that coats a portion of the fibers within the textile, disposed between the surface and the opposite surface of the textile, and in contact with the wire and the electrode;
wherein the wire, the electrode and the interconnect comprise an elastomer and metal particles.

In additional embodiments, a textile is a plasma-treated textile, a porous plasma-treated textile, or a porous plasma-treated nanotextile. In other additional embodiments the patterned electrically conductive wire is a serpentine patterned electrically conductive wire. In yet other embodiments the patterned electrically conductive wire can be any pattern that can adapt to the contours of any shape.

In various embodiments, the fibers comprise electrospun polyurethane. In additional embodiments, the textile has a pore size of about 1 micron to about 100 microns. In other embodiments, the surface and the opposite surface of the textile has coated fibers up to a depth of about 100 microns within the textile.

In various additional embodiments, the elastomer is a fluoropolymer or a fluorocopolymer. The fluoropolymer can be, for example, poly(vinylidene fluoride). The average molecular weight $M_w$ of the fluoropolymer can be about 400 kDa to about 700 kDa, about 500 kDa to about 600 kDa, or about 534 kDa (e.g., as determined by GPC). The fluorocopolymer can be, for example, poly(vinylidene fluoride-co-hexafluoropropylene), as shown in FIG. 1(e) wherein x and y are values such that the average molecular weight $M_w$ is about 200 kDa to about 600 kDa. The average molecular weight $M_w$ of the fluorocopolymer can also be 300 kDa to about 500 kDa, about 350 kDa to about 500 kDa, about 400 kDa, or about 450 kDa (e.g., as determined by GPC).

In various embodiments, the metal particles have a diameter of up to about 10 microns, for example, about 100 nm to about 10 microns, about 200 nm to about 10 microns, about 500 nm to about 5 microns, or about 5 microns to about 10 microns. To ensure effectiveness, the average metal particle size employed for a particular application should be less than the pore size of the textile substrate to which it is applied. Accordingly, in various embodiments, the metal particle size is smaller than the pore size of textile substrate. The Ag-particle size affects the depth of the ink permeation. The permeation of the printed ink can be optimized by employing suitable metal particle sizes.

In some embodiments the metal particles are transition metal particles, transition metal nanoparticles, transition metal flakes, or transition metal nanoflakes. In some embodiments, a fabric, fiber, particle composite, composite ink, textile, flake, pore, and clad can be (or are interchangeable with the terms) a nanofabric, nanofiber, nanoparticle nanocomposite, nanocomposite ink, nanotextile, nanoflake, nanopore, and nanoclad, respectively.

In other additional embodiments, the textile has an electrical resistance ratio of about 10 or less than 10 after about 1000 cyclic stretches from zero to about 30% strain at a rate of about 4% strain per second.

This disclosure additionally provides an ink composition comprising about 1 part to about 5 parts of (a) a fluorocopolymer, about 1 part to about 5 parts of (b) an organic solvent, and about 1 part to about 5 parts of (c) metal flakes. In various embodiments, the composition has a ratio of a:b:c of about 4:3:3. In additional embodiments, the metal flakes are silver flakes having a diameter of about 200 nm to about 10 microns, or about 1 micron to about 10 microns. In some other embodiments, the organic solvent is a ketone. In other embodiments, the copolymers disclosed herein can comprise random or block copolymers.

This disclosure also provides a method for fabricating a stretchable electronic textile from an ink composition described above or herein, comprising:
a) printing a circuit with the ink composition on a porous textile having fibers;
wherein a wire is printed on a surface of the textile, and an electrode is printed on the opposite surface of the textile;

b) inserting the ink composition into the textile to provide an electrical contact between the wire and the electrode, thereby forming a completed circuit;

c) drying the completed circuit;

wherein the printable ink coats a portion of the fibers that forms the completed circuit, and the textile has an electrical resistance ratio of about 10 or less than 10 after about 1000 cyclic stretches from zero to about 30% strain at a rate of about 4% strain per second.

In some embodiments, the fibers are electrospun polyurethane and the textile has a pore size of about 1 micron to about 100 microns. In yet other embodiments, the completed circuit comprises a circuit for a wearable medical device. In various embodiments the completed circuit comprises a circuit for sensing surface electromyography (sEMG), electromyography (EMG), electroencephalography (EEG), electrocardiography (ECG), electrooculography (EOG), respiratory rate, heart rate, mechanical strain, pressure, temperature, or vibration.

This disclosure provides additional embodiments of the disclosed e-textiles, including but not limited to, applications or use in electromyography (EMG), surface electromyography (sEMG), electroencephalography (EEG), electrocardiography (ECG), electrooculography (EOG), and other embodiments for respiratory rate, heart rate, mechanical strain, pressure, temperature, and vibration. This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

In one example we used commercially available nonwoven textile of electrospun polyurethane nanofibers, which are hydrophilic, thermoplastic, nonwoven electro-spun polyurethane (PU) fiber matrices. FIG. 1(c) shows a top-view scanning electron microscope (SEM) image of the PU textile. The fibers have diameters from one-order to four-order nanometers. There is a large number of pores within the fiber matrix. Such highly porous matrix allows the textile to have the abilities of high breathability, and absorbency from 2.5 to 18.5 g/g (i.e., absorbed liquid/textile in mass) when soaked in saline solution (0.9% NaCl in water) for 30 minutes when measured by following the NWSP 240.0.R2 (15) standard test (Technical Datasheet of SNS Nanosan®-Sorb material (42)). This PU textile is mainly used in medical applications as sweat and blood absorbent. Moreover, the textile has a stretchability up to 250% and good recovery below 50% when uniaxially strained.

The composite ink was prepared by mixing conductive silver flakes into fluoroelastomer matrix which is dissolved in methyl ethyl ketone (MEK) (or also known as butanone) as seen in FIG. 1(d). In literature, similar silver/fluoroelastomer composite inks were also reported for making stretchable conductors [cite Someya, Amit]. Firstly, the fluoroelastomer (obtained as DAI-EL® G-801 from DAIKIN AMERICA, Inc.) was dissolved in MEK in 24 hours. Then, silver flakes (obtained from Sigma Aldrich, average particle size of 2-3.5 microns) was added to the solution and stirred for 8 hours. The viscosity and conductivity of the composite ink depend on the concentration of the fluoroelastomer, and fraction of silver flakes. In one example of our work, the weight ratio of fluoroelastomer:MEK:silver flakes was chosen as 4:3:3. Each integer of this ratio can independently be increased or decreased by one or two integers to provide other suitable ratios.

For printing, the textile substrate with thickness of 300 microns was pre-treated in a plasma chamber for 10 minutes. The prepared viscous ink was loaded to a syringe of jet-printing system (commercial product as nScrypt Tabletop-3Dn printer). Ink droplets were expelled via a 150-micron nozzle under a pressure of 10 kPa relative to air pressure. Upon depositing on the textile substrate, the ink microdroplets were absorbed from the surface to the inside structure of textile. Interestingly, the hydrophilic fibers were wetting with the viscous ink, which then dried to form a very thin coating layer of ink along the fibers as shown in FIG. 1(e-i). Printed conductors were dried at room temperature of 22° C. in a fume hood for 8 hours. FIG. 1(g) shows that the ink-printed structure had roughly a total thickness of 140 microns, of which comprising of two parts such as (i) an 80-micron-thick layer atop the textile surface, and (ii) another 60-micron-depth permeated layer inside the textile. For the permeated part, the silver flake/fluoroelastomer composite ink formed coating clads of the fibers as shown in illustration of FIG. 1(f). The coating clads were observed to have an average thickness in sub-micron dimension, in which the silver flakes continuously aligned to create intrinsically stretchable conductive paths along the fibers, as shown in the SEM image (FIG. 1(h)). Such conductive cladded fiber interconnects can benefit the mechanical durability, conductivity, and adhesion of conductors to the textiles. These advantages play key roles in performance of e-textiles when integrated to a full electronic system. In another example the printing process as described above was demonstrated on commercially available woven Nylon and Spandex textile substrates. No marked change in printing performance or overall e-textile performance characteristics were observed.

Effects of Ag particles on permeation of composite ink into textiles. We used two species of Ag particles with different shapes and particle sizes, including: i) flakes with the size of about 10 μm metal traces (denoted as Ag flakes hereafter) and ii) powders with size of about 2-3.5 μm metal traces (denoted as Ag powders). The size values are stated as specified by the vendor (Sigma-Aldrich); however, the actual size distribution of individual particles (flakes or powders) was extremely polydisperse in nature. Especially, the existence of nanosized particles seems to affect the properties of e-textiles. The SEM image of the Ag flakes reveal that each particle is predominantly larger than a micrometer in size with irregular shapes (FIG. 10a), whereas many particles in the Ag powders had sizes around (or even less than) 200 nm (FIG. 10b). These small particles efficiently permeate into the pores of the textile substrate, resulting in the formation of cladded-layer shown in FIG. 1f, h. FIG. 10c,d shows the cross-section of the printed inks (i.e., Ag particles with fluoropolymers after solvents were dried). The printed ink containing Ag flakes showed distinctively smaller thickness of cladded-layer (FIG. 10c) when compared to the printed ink with Ag powders (FIG. 10d).

Figure 10:
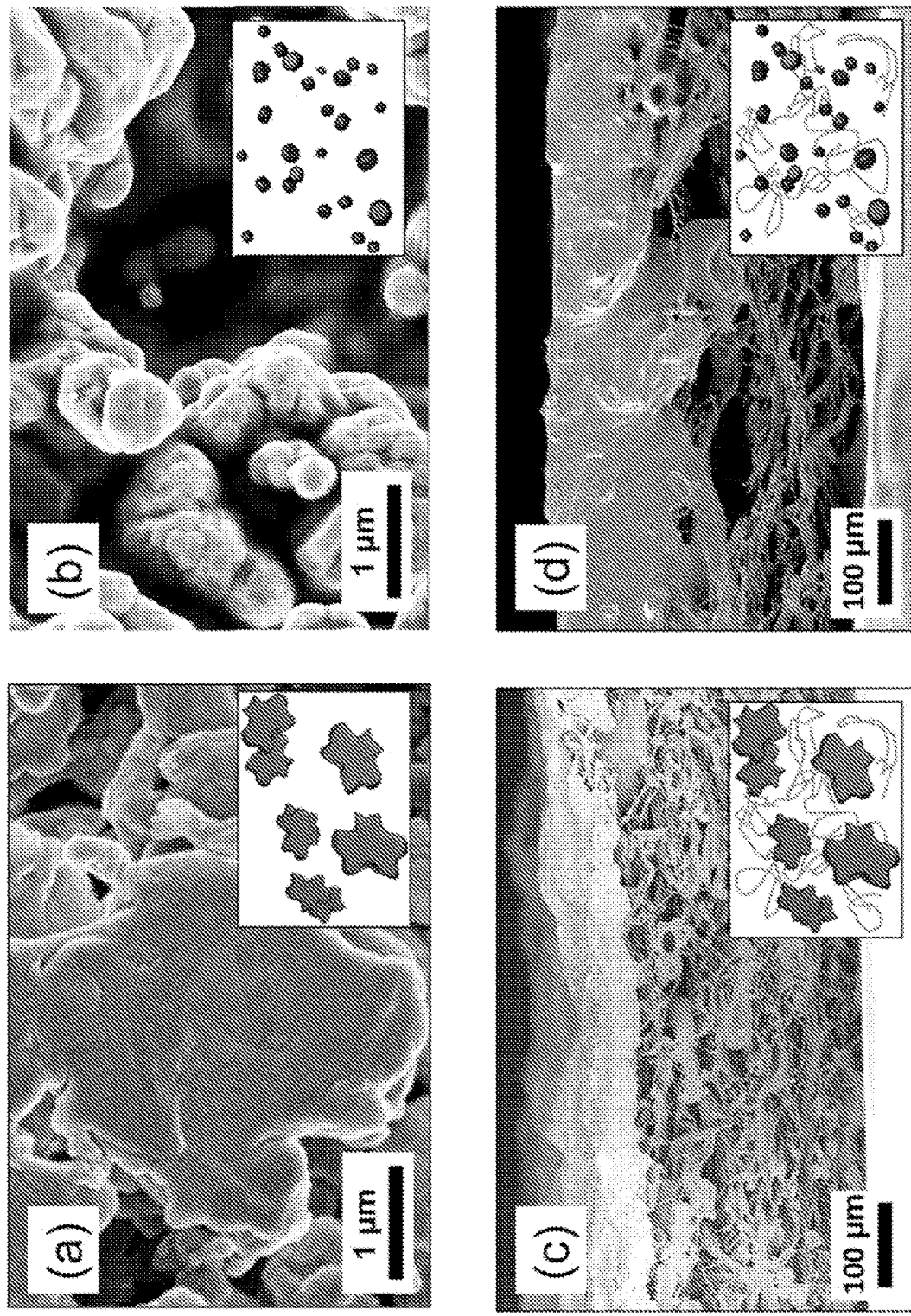
FIG. 10. Metal flake size and permeation effect.

In our experiment, viscosity, ink-jetting parameters, and solvent drying rate were essentially the same for the two types of inks, but the permeation depth showed a stark difference. Additionally, when composite materials are printed into a porous substrate, one must take the size effect of printing particles and the pores in the substrate into account. As shown in FIG. 10c,d, Ag-powder-based ink contains many small-sized particles that can freely pass through the pores opening through the forest of nanosized fibers in the substrate, whereas Ag-flake-based ink does not. As a result, the Ag-powder-based ink was able to form a cladded layer of around 60 µm in thickness (FIGS. 1h and 10), whereas that of Ag-flake-based ink was only around 10 µm thick (FIG. 10c). We believe that such geometric effect dictated the difference in the permeation depth of the wet ink, which finally caused the thickness of the cladded-layer.

Figure 2:
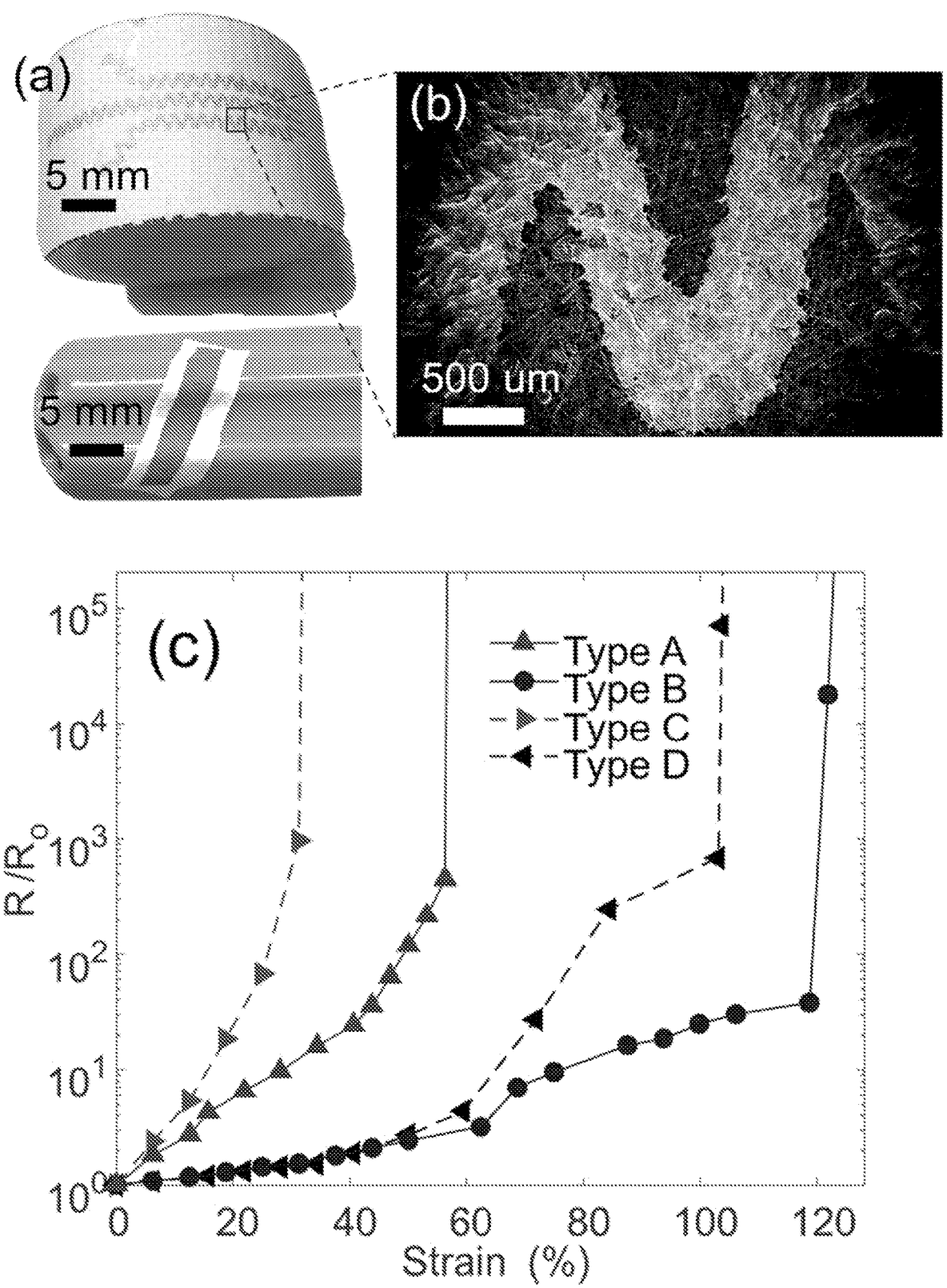
FIG. 2. Stretchable fabric-based interconnects by printed Ag-particle composite onto electro-spun polyurethane textile.
Figure 2:
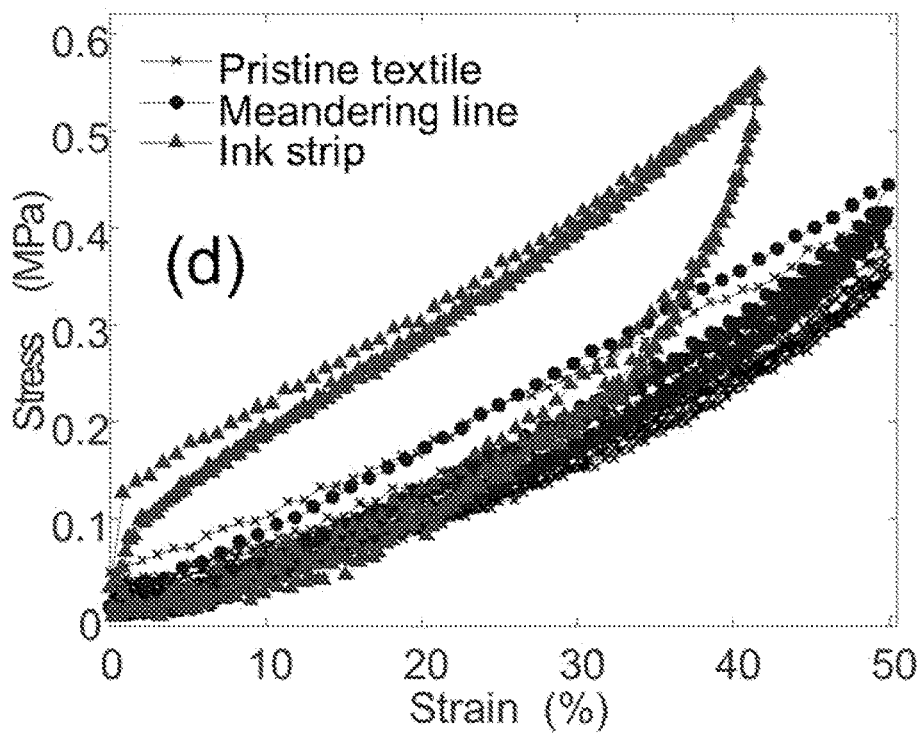
Figure 2:
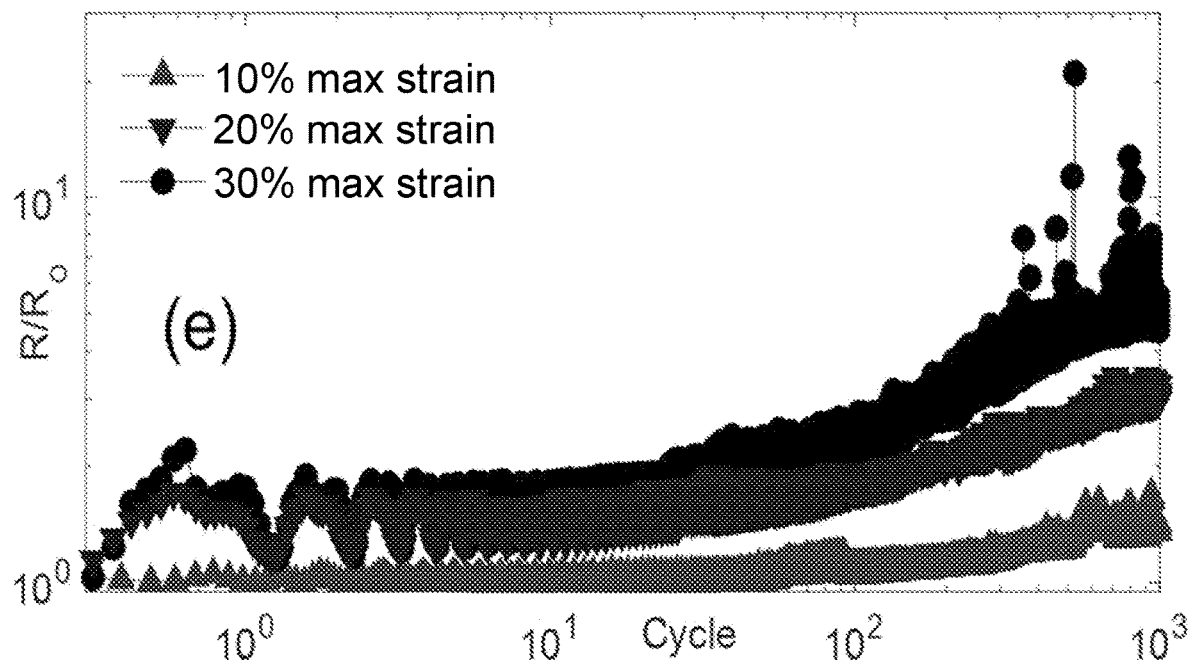
Figure 2:
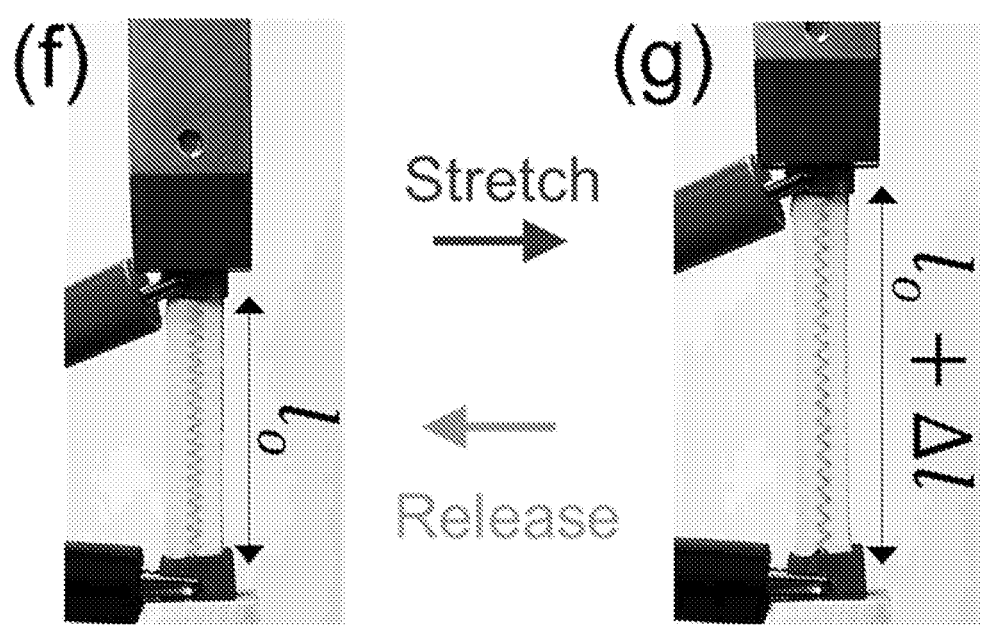
Figure 7:
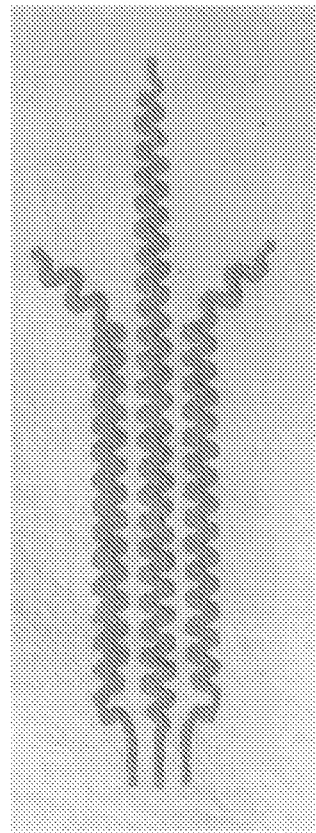
FIG. 7. A composite ink vs. commercial ink.
Figure 7:
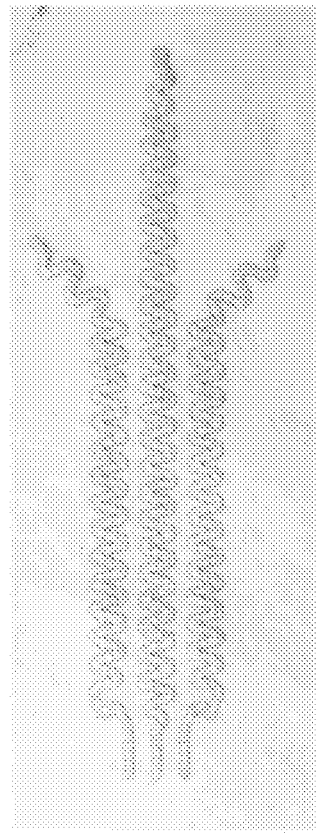
Figure 8:
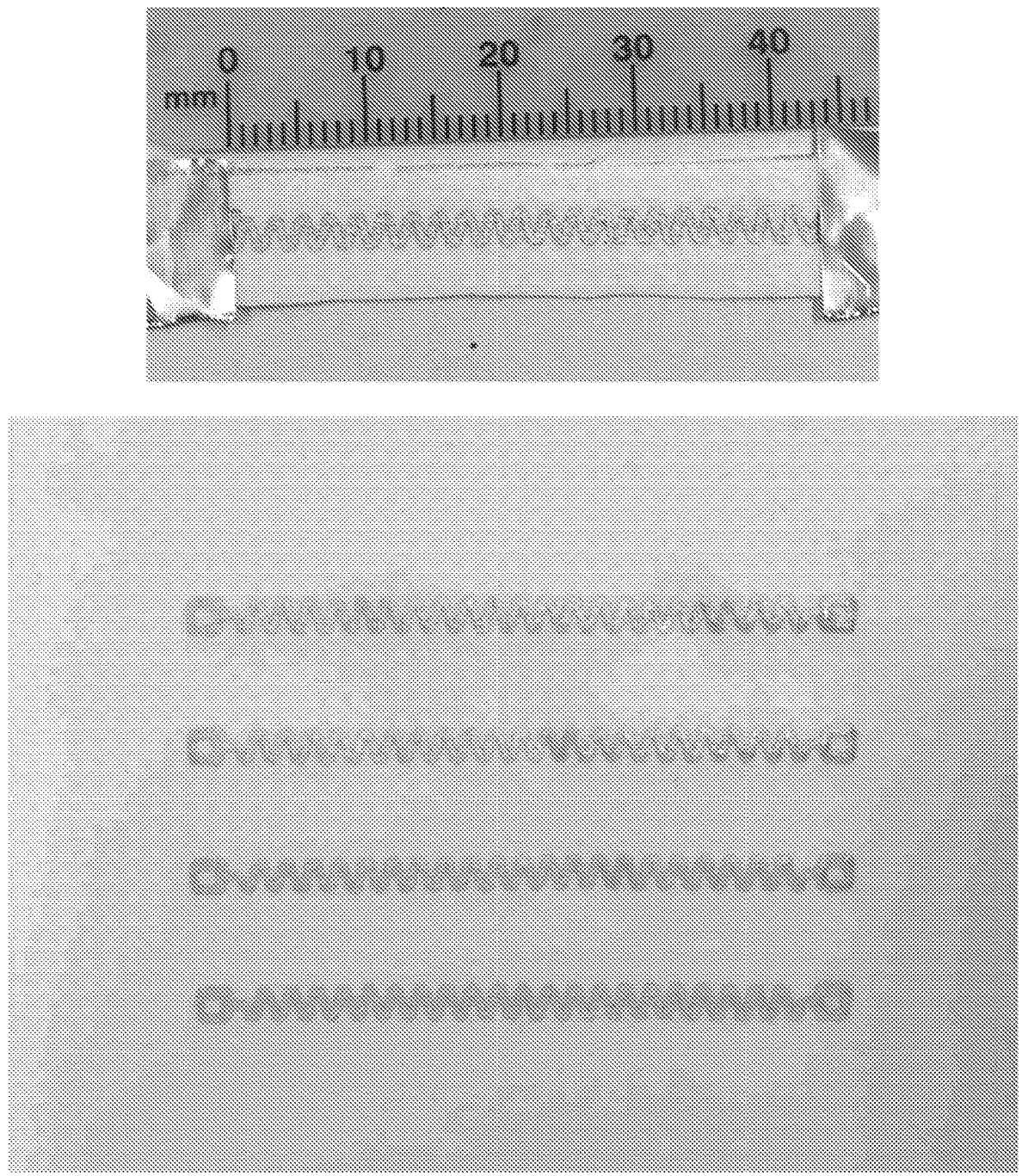
FIG. 8. Serpentine interconnects.

Electrical and Mechanical Characteristics. We studied the mechanical and electrical performance of the cladded interconnects by printing the ink on the textile for two different designs such as a narrow rectangular strip, and a serpentine line as shown in FIG. 2(a, b). In addition, commercial silver ink with silver particle size more than 10 microns was also printed on the same textile for comparison (see FIG. 7). The dimension of the narrow strip as 1 mm width and 40 mm length, and that of the serpentine line was 0.5 mm linewidth, 2 mm lateral amplitude, 40 mm length, and 2 mm pitch interval (FIG. 8).

FIG. 2(c) shows the change in resistance under uniaxial strains from zero to 125% of four printed conductors which are named as Type A and B for a narrow strip and a serpentine line of the composite ink, and Type C and D for the same designs of the commercial ink. The printed composite ink has demonstrated better electrical properties than the commercial ink did (FIG. 2(c)). The relative resistance ratio of the composite ink increased 412 times at 60% strain for Type A, and 24.7 times at 120% strain for Type D. For the commercial ink, the resistance ratio increased 1000 times at 30% strain for Type C, and 920 times at 100% strain for Type D. It was observed that the serpentine samples have enhanced the electrical properties under stretching for both printed conductors, i.e. composite and commercial inks.

The printed samples of the composite ink were tested under 5 stretching-releasing cycles of uniaxial tensile strains from 0% to 50%. As shown in FIG. 2(d), hysteresis is observed for the five loading-unloading cycles for the printed narrow strip. However, for the serpentine sample, after the first cycle, the hysteresis reduced to be negligible. Similar behavior was also observed for the pristine textile strip. In addition, both the printed samples, i.e. narrow strip and serpentine line, showed 100% self-recovery without distinct yielding in the stretching-releasing cycle. Therefore, it indicates that the printed samples would have high fatigue resistance, or mechanical durability. FIG. 2(e) shows cyclic durability of the electrical properties of the composite serpentine lines under a thousand loading-unloading cycles of 10%, 20%, and 30% stretching with a rate of 4%/second. The resistance gradually increased with the number of stretching cycles. However, the relative ratio of resistance was maintaining at small value below 10 times for all of the cyclic stretching values of 10%, 20%, and 30%. Such performance was achievable due to the well cladding of the composite ink and the fibers, and the enhanced stretchability of the serpentine shape (FIG. 2(f, g)).

Figure 3:
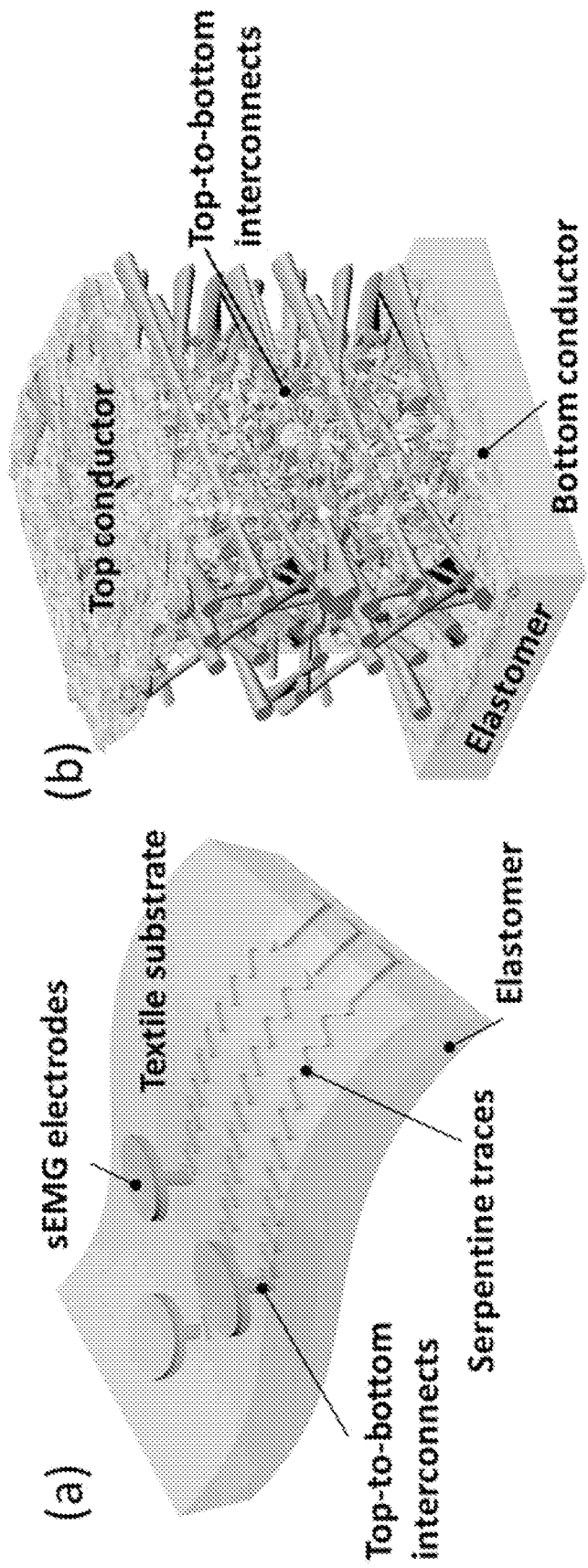
FIG. 3. Two-sided printed fabric devices with EMG sensors and serpentine interconnects.
Figure 3:
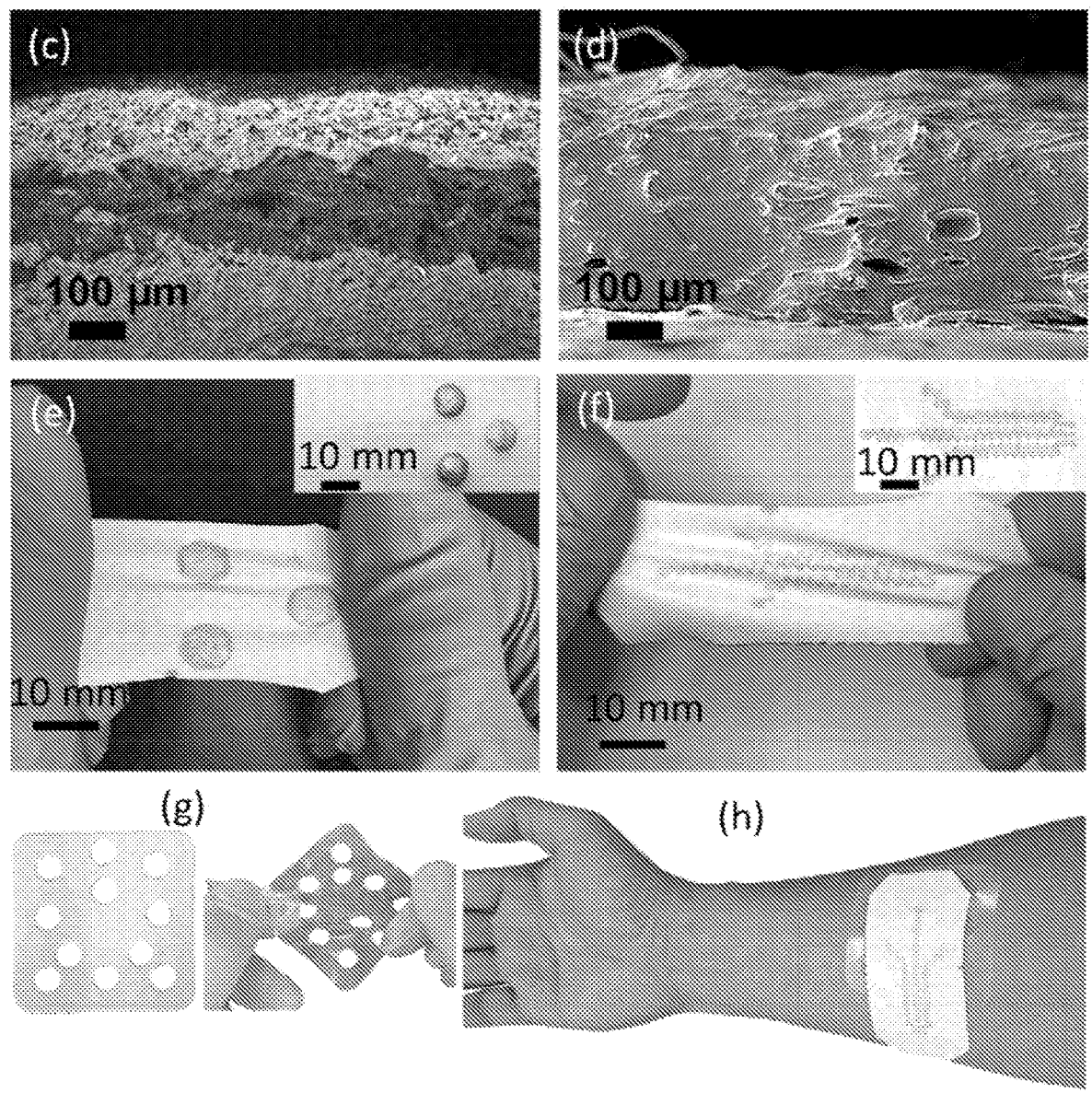

Stretchable, Two-Sided Integration E-Textiles. The printed ink which consisted of a part atop the textile surface and another part cladding the fiber was a stretchable and robust textile-based conductor. It is observed that the ink permeated partly into the textile so that the fiber cladding depth was around a quarter of the textile thickness as seen in FIG. 1(g). We exploited this to make a fully printed, two-side e-textile of biosensors as shown in FIG. 3. The biosensors consisted of electrodes and serpentine interconnects that were printed on opposite sides of the textile. Utilizing the porous textile structure, narrow conductive channels were embedded inside the textile to be top-to-bottom interconnects between the electrodes and the on-surface interconnects as shown in FIG. 3(a, b). The narrow channels were formed by injecting a small amount of the ink into the textile spacer between the electrodes and the serpentine interconnects via a needle (0.3 mm diameter). FIGS. 3(c) and (d) shows the SEM images of the cross sections of the printed electrode and the narrow conductive channel.

Figure 9:
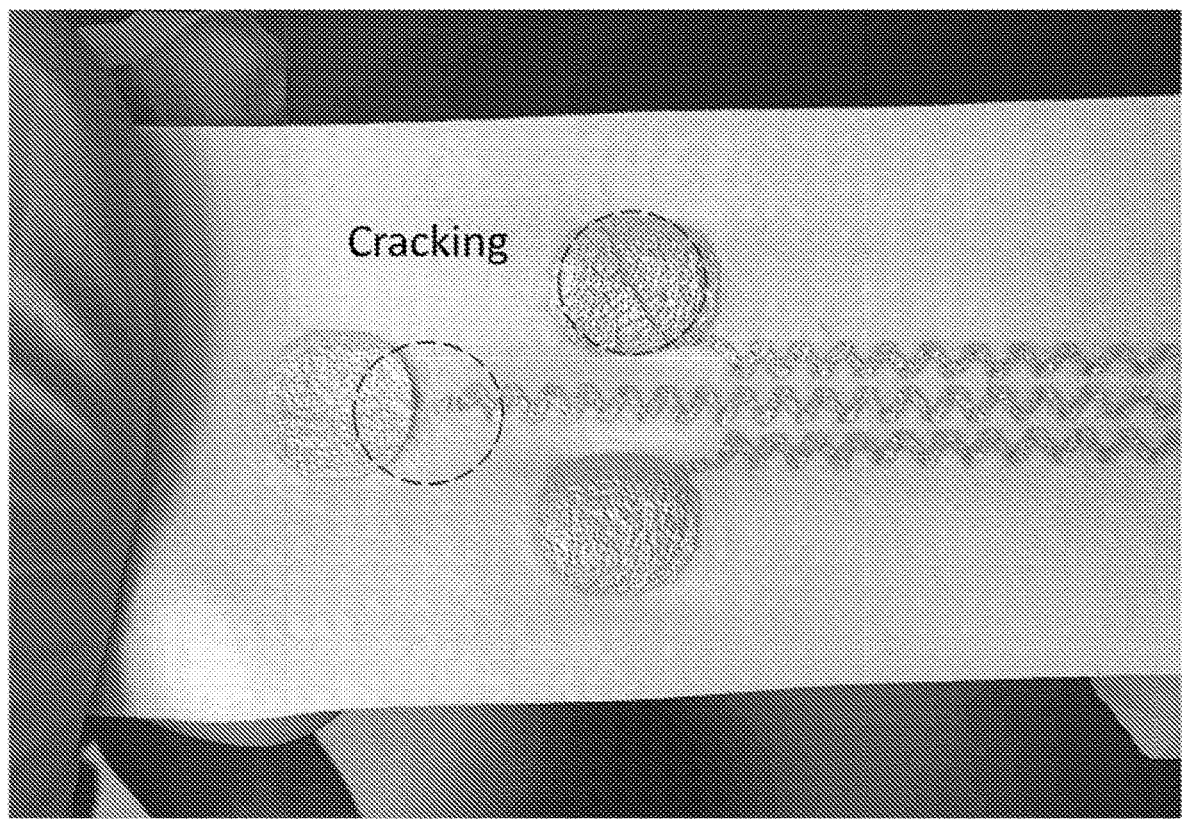
FIG. 9. Failure of commercial ink.

Moreover, e-textiles that have electrodes and wires on the same side are prone to suffer ink cracking at the electrode-interconnect junction as shown in FIG. 9. This issue happens due to the mismatch in stiffness since the electrodes are large-area pads and stiffer than the serpentine interconnects. Therefore, the two-sided e-textile resolves the unstable connection. The narrow channels are intrinsically stretchable so that it benefits a stable connection between the electrodes and the wires. FIG. 3 (e, f) shows that the fully integrated two-sided e-textiles are under harsh stretching. The e-textile biosensors were conformally attached onto skin by a medical double-sided adhesive tape. For direct contact of electrode-to-skin and breathability, the adhesive tape was patterned with several cut-through circles (FIG. 3(g, h)).

Figure 12:
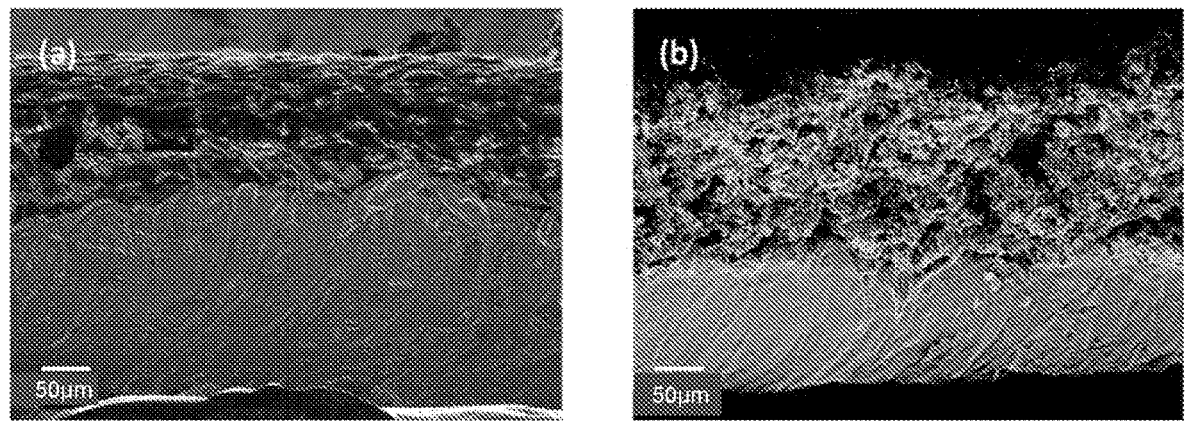
FIG. 12. Effect of heatless compression treatment on e-textile.
Figure 12:
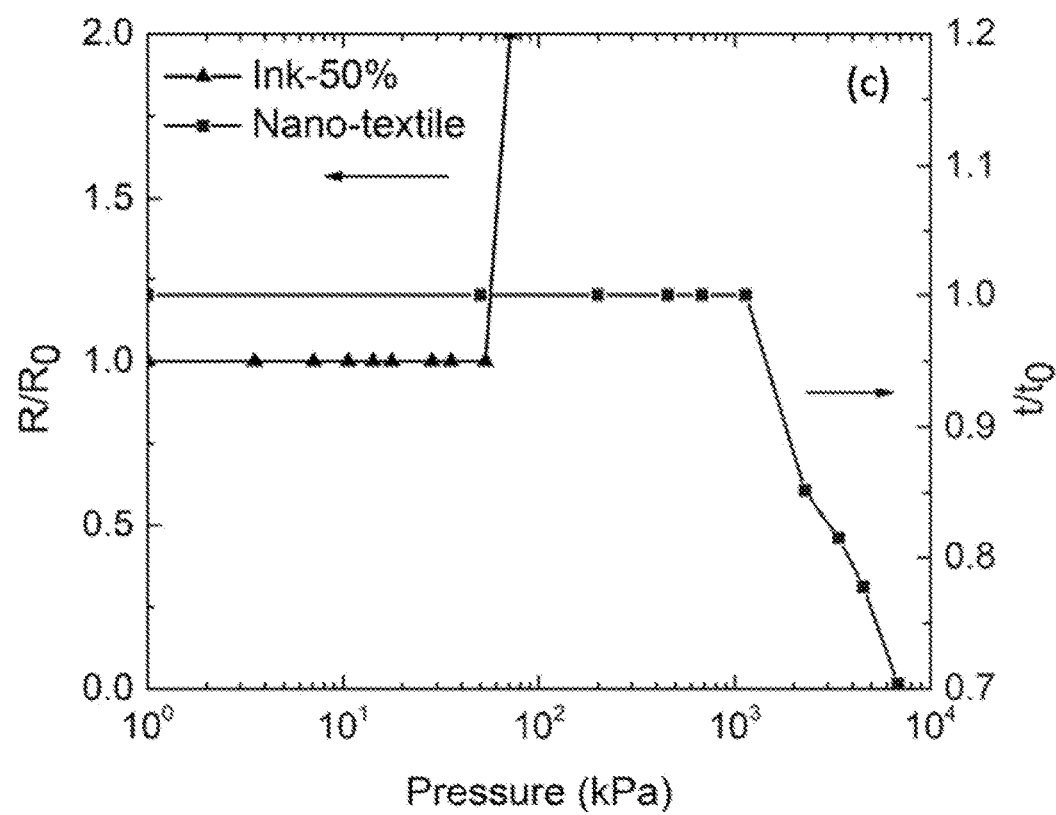
Figure 12:
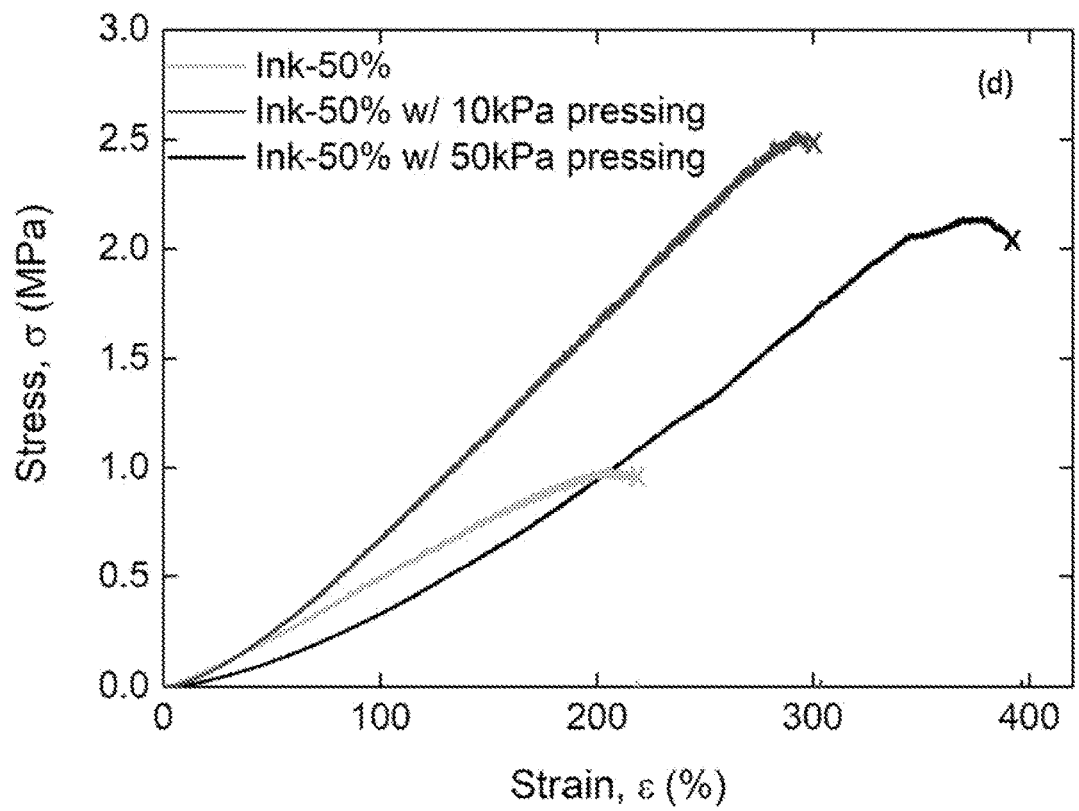
Figure 12:
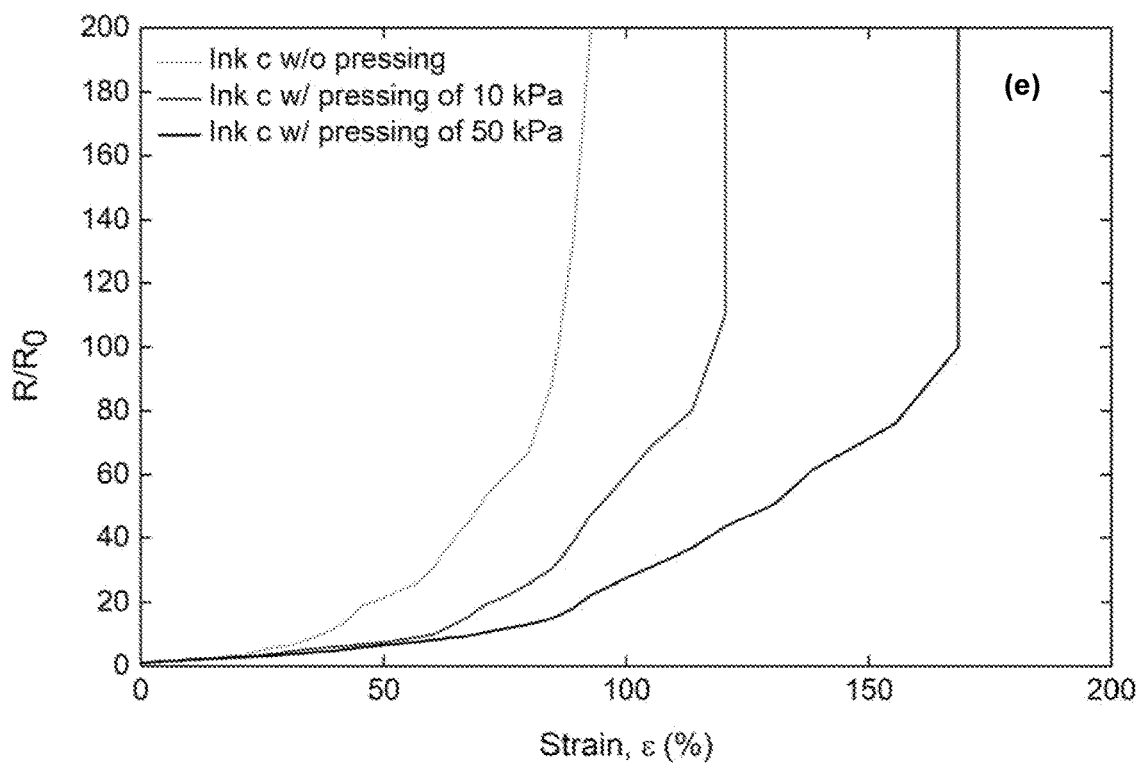

Squeezed, One-Sided Construct of E-Textile for Enhanced Stretchability in Selected Areas. In selected areas of the aforementioned sample, it is advantageous to apply compressive pressure (squeezing) for 10 minutes without applying heat. In some embodiments, the compressive pressure (squeezing) can be high compressive pressure (strong squeezing), for example, pressure of about 5 kPa to about 52 kPa, about 10 kPa to about 50 kPa, about 10 kPa to about 25 kPa, or about 25 kPa to about 50 kPa. Such squeezing treatment causes a fundamental change to the internal morphology of the e-textile, leading to improved mechanical and electrical properties of the printed textiles. Here, the pressing was done 5 minutes after printing; in other words, the printed region of the nano-textile substrate was still wet and swollen with the solvent. As a control experiment, we evaluated the structural compression resilience limit of pristine nano-textiles. The nano-textile substrate could retain its original thickness, as well as its porous non-woven fibrous structure, after removing the pressure when the applied pressure was up to 2280 kPa (FIG. 12c). For Ink-50% printed textiles, however, the electrical conductivities of the strip-printed textiles were irreversibly degraded when the applied pressure reached ~53 kPa (FIG. 12c). Thus, we compared the effect of applied pressures of 10 kPa and 50 kPa on the Ink-50% printed nano-textiles.

The squeezing treatment caused a fundamental change in the internal structure of the printed textile. Before squeezing, the printed textile showed tri-layer structures; with a strong presence of ~75 µm-thick dried ink 'skin' at the top, the cladded layer with the permeation depth showed 28±2 µm, whereas the non-permeated part of nano-textile remained as pristine status (qualitatively similar to the structure shown in FIG. 1g). The cross-sectional helium-ion microscopy (HIM)

images of FIGS. 12a and 12b demonstrate printed samples post squeeze treatment, where applied pressures of 10 kPa (FIG. 12a) and 50 kPa (FIG. 12b) were used. FIGS. 12a and 12b demonstrate that the squeeze treatment fundamentally alters the cross-sectional morphology into a distinct two-layer structure. Here, the top layer consists of rich content of silver, whereas its thickness is 106±6 μm at pressure of 10 kPa and 188±8 μm at pressure of 50 kPa. Interestingly, the bottom layer no longer showed fibrous structure of the nano-textile substrate, which were preserved in cladded layer as described in FIGS. 1g-h, 2a-c, 3c, and 10c-d. Instead, the nano-fibers seemed to be fused together by permeated fluoroelastomer.

In some embodiments, the bottom layer can comprise a fibrous structure wherein fibers of the textile are amalgamated by a polymeric additive. The polymeric additive can be an elastomer such as, for example, polyisoprene or ethylene-vinyl acetate, or a fluoroelastomer, for example, one or more of hexafluoropropylene (HFP), vinylidene fluoride (VDF or VF2), tetrafluoroethylene (TFE), vinylidene fluoride (VDF), hexafluoropropylene (HFP), perfluoromethylvinylether (PMVE), copolymers of hexafluoropropylene and vinylidene fluoride, terpolymers of tetrafluoroethylene, vinylidene fluoride and hexafluoropropylene, or polytetrafluoroethylene.

The strain to failure with applied pressures of 10 kPa and 50 kPa were increased to 306% and 397%, respectively, compared to the without-pressure value of 221% (FIG. 12d). At the same time, the tensile moduli decreased from 2.292 MPa to 1.622 MPa, then to 0.694 MPa, with increasing applied pressures from zero to 10 kPa, then to 50 KPa. The strain tolerance for electrical conductivity was significantly improved (FIG. 12e). These improved mechanical and electrical properties with applied pressure are possibly due to the altered structures of nano-strands in the e-textile (fusion of the strands).

Figure 13:
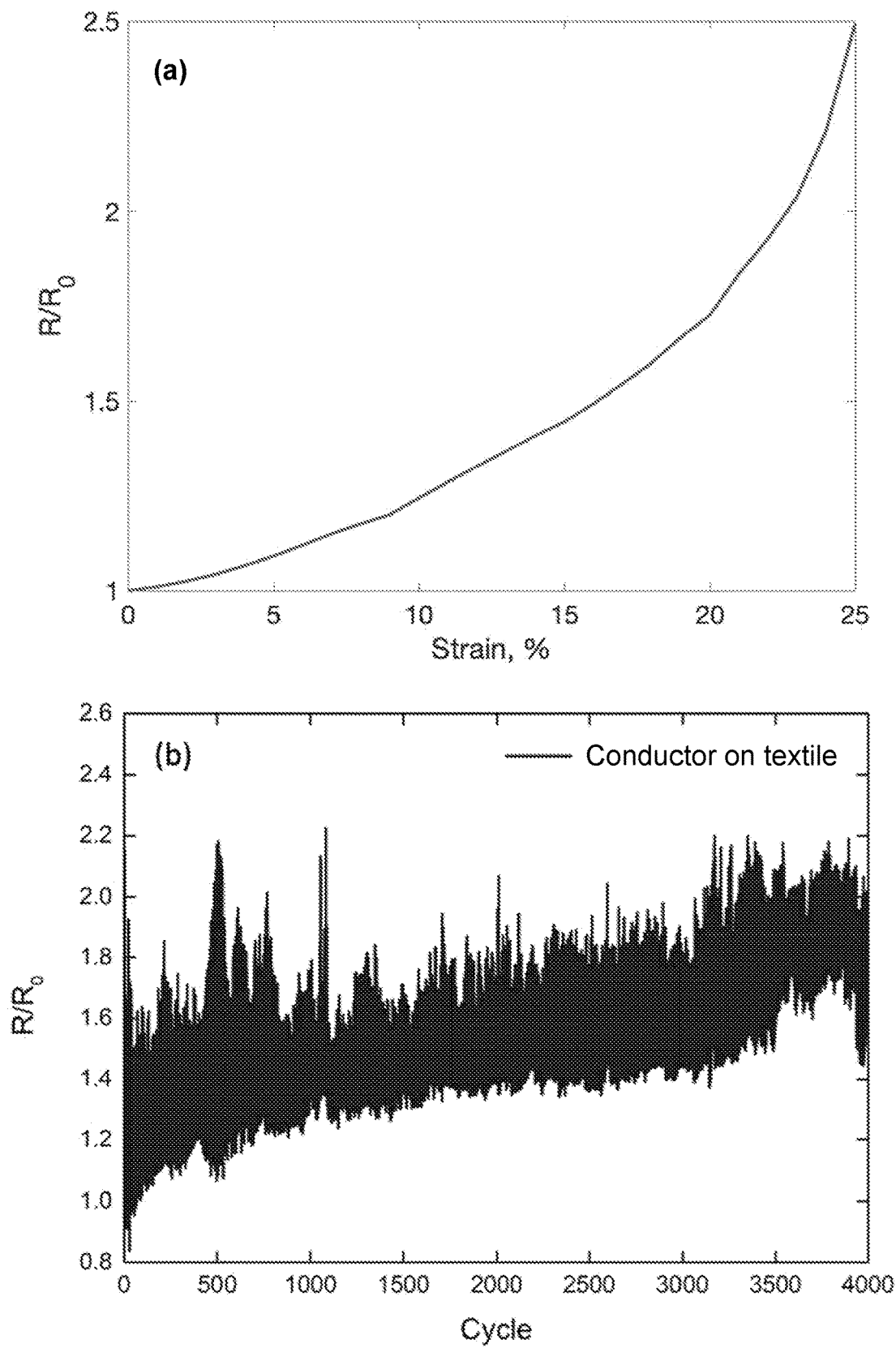
FIG. 13. E-Textile strain sensing performance characteristics.

E-Textile System for Strain Sensing Application. The stretchable e-textile may be adapted for use as a mechanical strain measurement system, which may be further applied to measure and monitor biomechanical parameters. Strain sensors were fabricated (30 identical samples) using the printing method disclosed herein and were subjected to sensitivity and reliability testing. FIG. 13a demonstrates the exponential growth of relative resistance to increasing strain (0%-25% strain, 1 sample); thus, providing a convenient means of monitoring biomechanical motion (e.g., dynamic joint angle). The reliability results demonstrated in FIG. 13b show an increase in unstrained resistance of less than 2.5 times after each sample was subjected to 4000 cycles of 20% uniaxial strain loading.

Fully Integrated E-Textile System for Surface Electromyography (sEMG) Application. The two-side e-textile biosensor was connected to an electronic circuit for sEMG monitoring system with real-time wireless communication to computer/smart phone/portable tablet (FIG. 4(a)). The e-textile sEMG system is fully portable, lightweight, compact, and worn on human body by the patterned medical adhesives (FIG. 4(b)) The electrode side of the e-textile adhered well and conformed to skin, whereas the serpentine communication lines were on the other textile side, thus separated from unnecessary contact with skin. Therefore, the sEMG signal is protected from noise and crosstalk artifacts. Moreover, the conformity of the e-textile can benefit the suppression of unwanted signals from body movements that are not associated with the muscles of interest when measuring.

Figure 4:
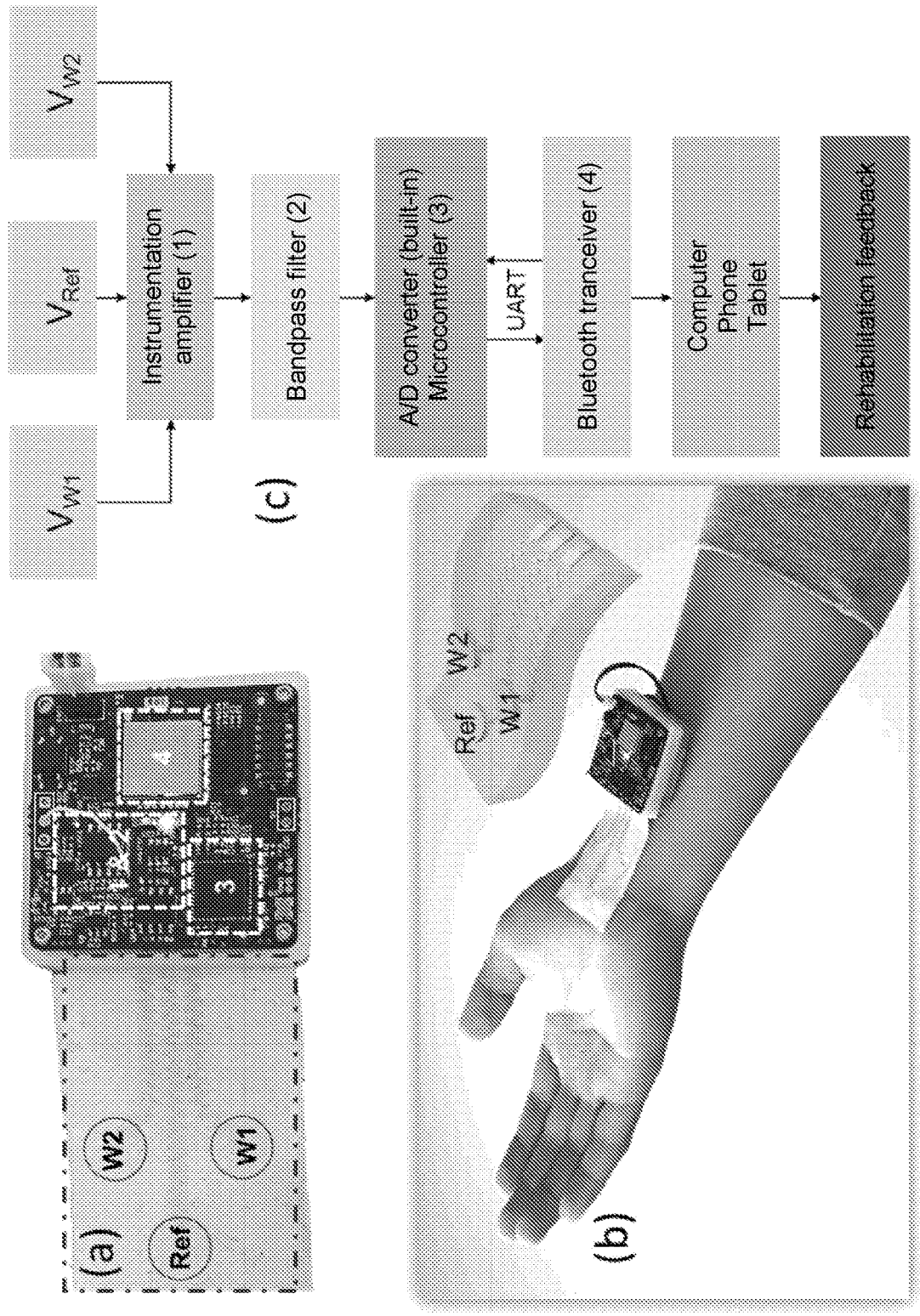
FIG. 4. Fully integrated e-textile sEMG devices for real-time monitoring muscle activities.

FIG. 4(c) shows the system-level schematic of the signal transduction, filtering, processing, and transmission to real-time monitor muscle activities. The signal of the sEMG biosensors was amplified with analog circuit to finely stay in the input voltage period of the analog-to-digital (A/D) converter. Then, the microcontroller regulated the converted signal and relayed it to the Bluetooth transceiver. The wireless signal was sent to a computer or mobile interface for further analysis.

sEMG Monitoring of Muscles Activities. The e-textile sEMG system was worn on various body areas of a participant to monitor activities of different muscles (FIG. 5(a)). There are four body areas of interest including the (i) submental area, (ii) elbow, (iii) calf, and (iv) ankle. For each area, the reference electrode was located on the bone regions for robust measurement as following the study of Dr Chung & Dr Rieger et al. (2016).

Figure 5:
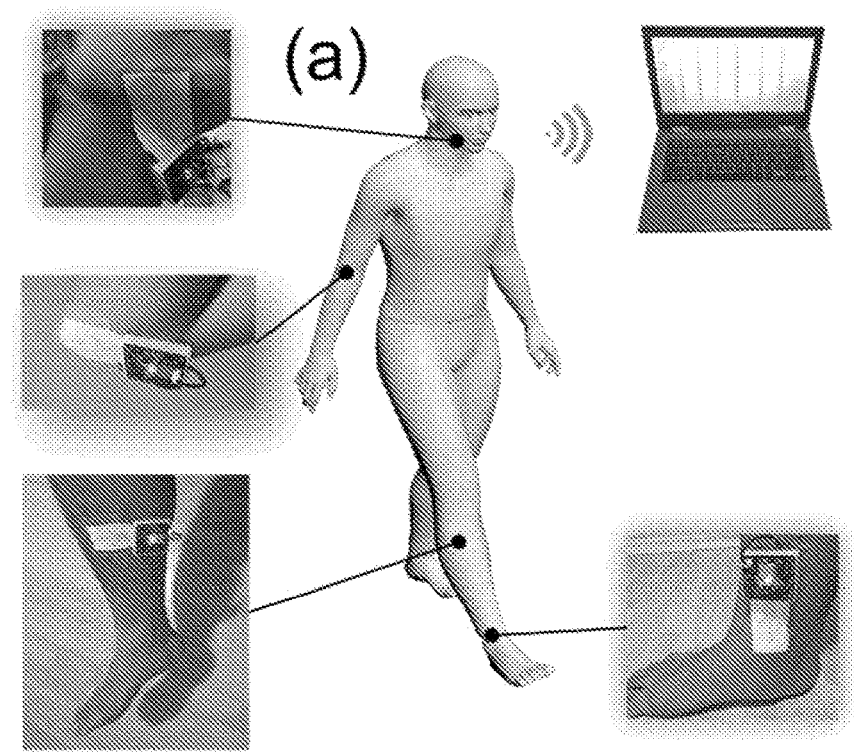
FIG. 5. sEMG measurements of muscles activities.
Figure 5:
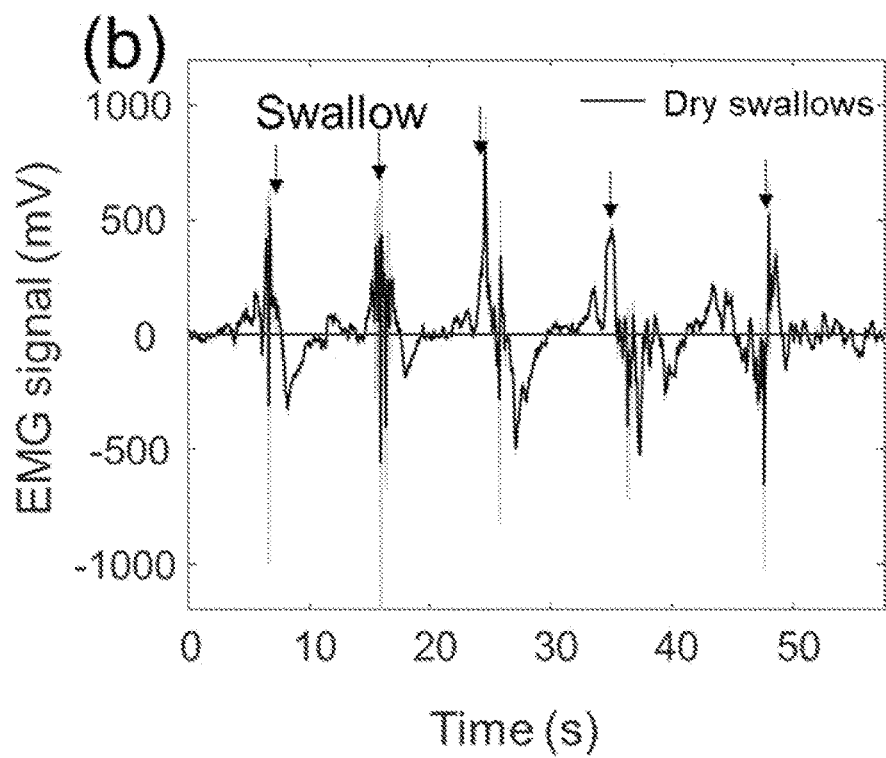
Figure 5:
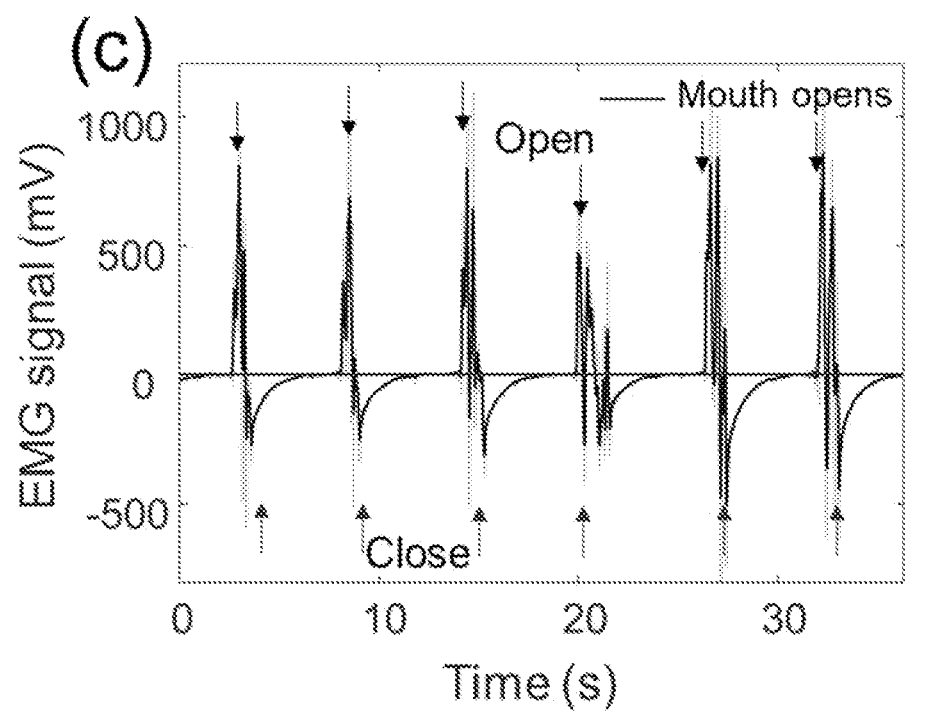
Figure 5:
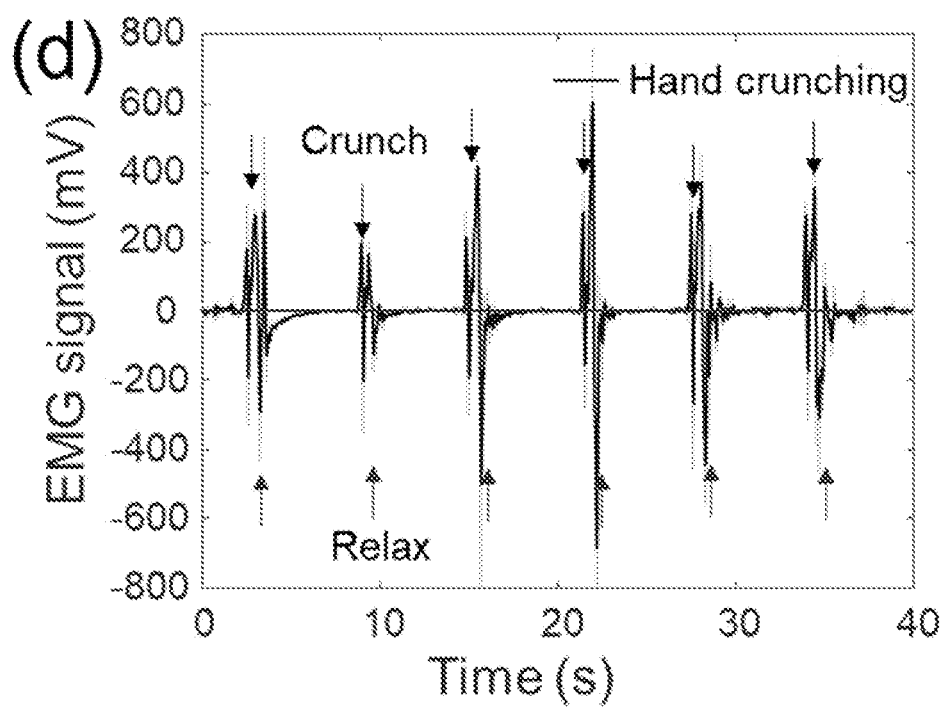
Figure 5:
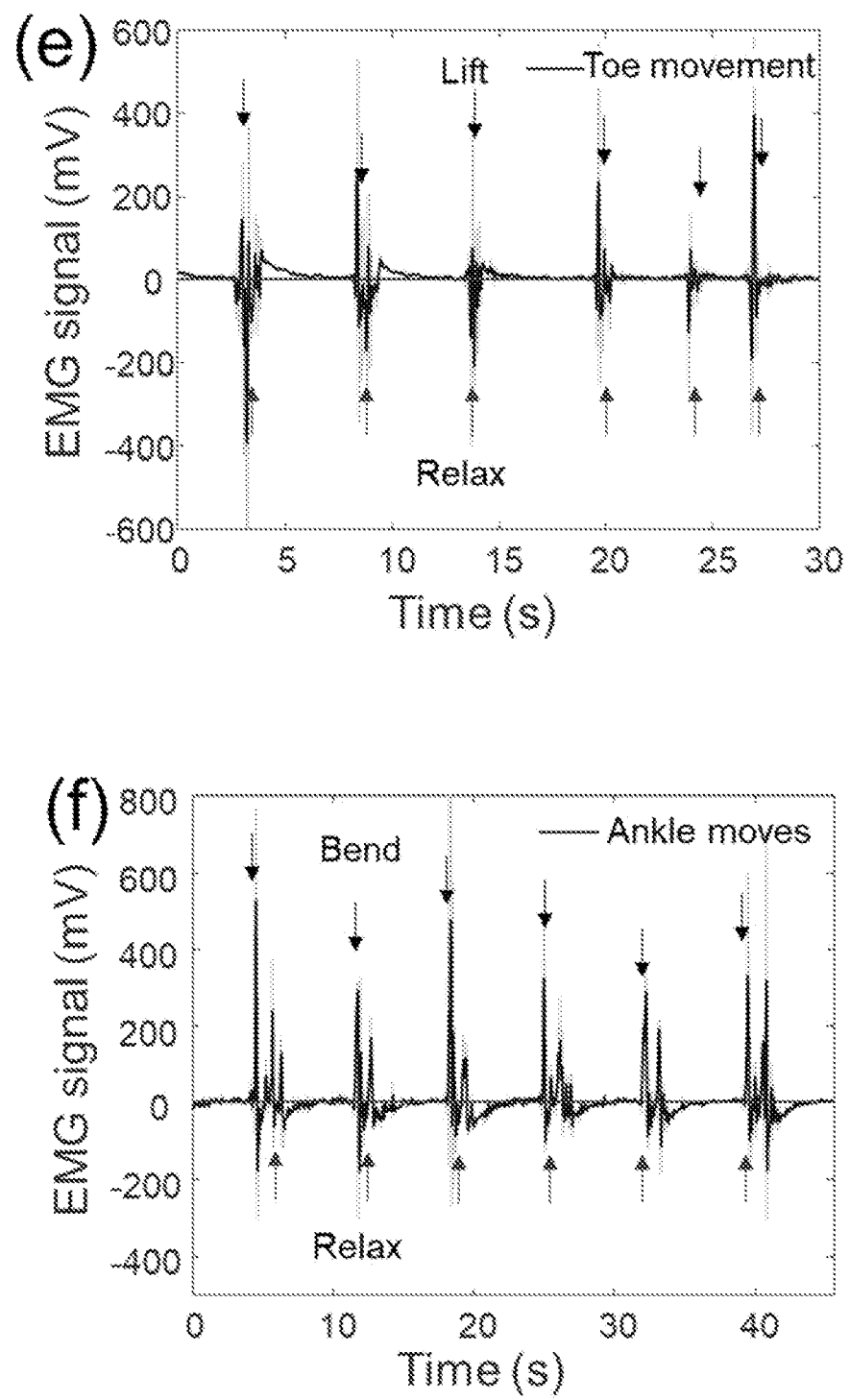

For the sEMG assessments of the submental area, we monitored two activities: saliva swallowing, and mouth opening/closing separately. The participant was asked to swallow saliva for 5 times, then separately to open and close mouth for 5 times. During the swallowing incidents, FIG. 5(b) shows the signal to surge to 0.5 V then shortly reduced to −0.5 V. FIG. 5(c) shows the signal during mouth opening and closing events. It was clearly observed that the general shape of the swallowing signal is distinct from that of the mouth opening/closing one. In fact, notable peaks of the signal for both events were observed.

For recording the hand crunching events, the sEMG system was located on the elbow of the participant. The participant was asked to hold the hand close and then crunch/relax. FIG. 5(d) shows that the crunching peaks were recorded with high amplitude of 0.6 V, followed by −0.6 V for hand relaxing. Similarly, the signal of lifting toe from the calf (FIG. 5(e)) and that of ankle bending from the ankle (FIG. 5(f)) were also recorded with the short burst of signal shape. In general, the sEMG signal had the distinguishable shape for different muscles and their activities.

In this work, an e-textile was developed with improved mechanical durability and electrical performance, by jet-printing a composite ink to form ink-cladded conductive fibers inside the textile. The ink-cladding is possible because the composite ink with silver flakes was absorbed by the hydrophilic fibers and vast number of pores inside the textile. As a result, the printed serpentine interconnects had a conductivity of 3000-4000 S/cm, and their resistance ratio only increased up to 10 times when cyclic stretching under 10%, 20%, and 30% uniaxial strains. Moreover, the e-textile was used to fabricate a fully printed, double-size, stretchable electronic system for sEMG and other applications. We anticipate that the e-textile with composite ink in couple to textile can open new opportunities of engineering innovative, practical wearable health care.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Composite Ink Preparation

Fluoroelastomer (DAI-EL G801, Daikin Industries) and butanone (Sigma Aldrich) were mixed with weight ratio of 1:2.55. After stirring with a magnetic stirrer for 6 hours, silver flakes (Sigma Aldrich, average particle size of 2-3.5 µm, ≥99.9% trace metals basis) were added to the solution in a 2.5:1 (silver:fluoroelastomer) weight ratio and mixed with magnetic stirrer for 4 h. 10 minutes sonication was applied to the solution to get well-dispersed stretchable silver ink. All procedures are carried out at room temperature.

Example 2

Printing of Composite Ink

Figure 6:
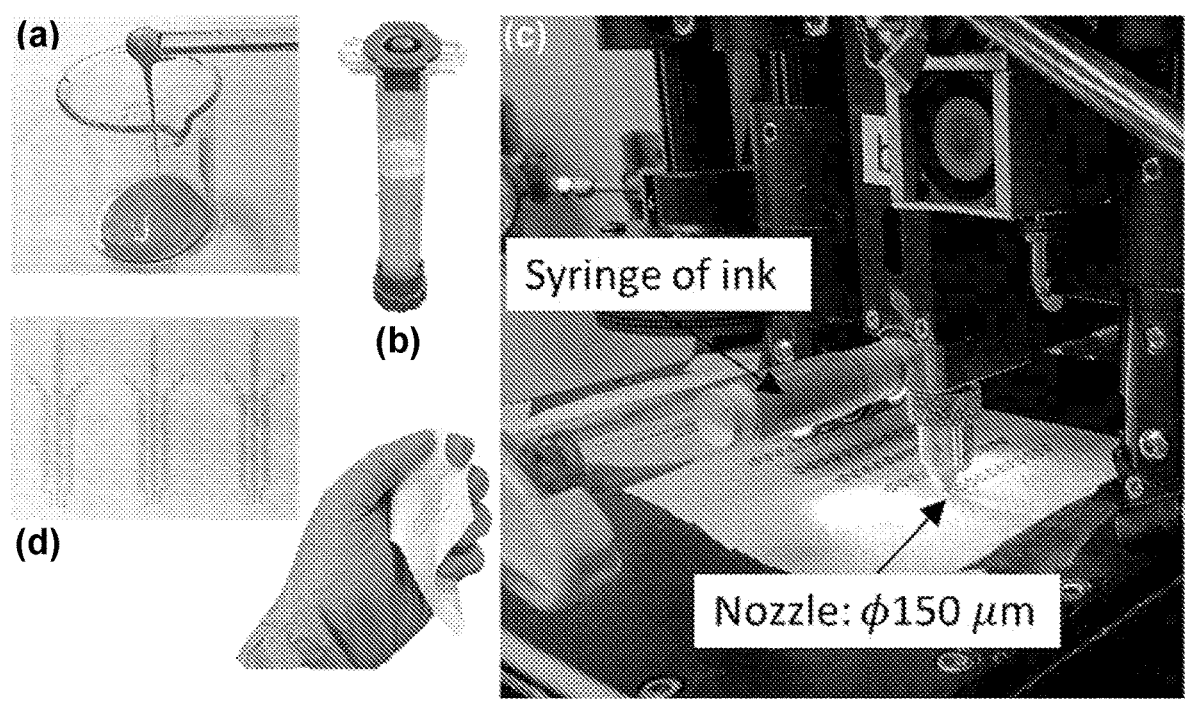
FIG. 6. Viscous ink printing setup and apparatus, including sample ink, loaded syringe, printer, and resultant printed textile.

The prepared ink (FIG. 6a) was loaded to a syringe (FIG. 6b) which is specifically designed for the nScrypt Tabletop-3Dn printer (FIG. 6c). A sheet of electrospun polyurethane nanofibers (Technical Datasheet of the material, see (42)) was cut in a rectangular shape of 120 mm×120 mm and pre-treated in oxygen plasma for 10 mins. The textile sheet was placed in the printer bed which was kept at room temperature during printing. To print the stretchable interconnects, the prepared ink was loaded to a syringe. For one-time printing, an amount of 10 mL was used. The printed sample (FIG. 6d) was dried in vacuum chamber at room temperature for 8 hours.

Example 3

Double-Sided E-Textile Biosensors

After printing and drying, the samples which were printed on one side were flipped to the other side and loaded to the printer. The samples were carefully positioned by a laser marking of the printer to achieve well aligned two-side circuit. After printing the circuits on two side, via interconnects (from one to another side) were formed by using a very small needle (3/8" diameter) that was dip-coated by the prepared ink to puncture through the thickness of the textile one-time. The double-sided e-textile can be used for a surface electromyography (sEMG) system to monitor muscles activities or an electroencephalography (EEG) system to record brain waves. Other biological sensing applications of the e-textile include, for example, electrocardiography (ECG), electrooculography (EOG), respiratory rate, heart rate, mechanical strain, pressure, temperature, and/or vibration sensors.

CITATIONS

1. Stoppa, M.; Chiolerio, A. Wearable Electronics and Smart Textiles: A Critical Review. Sensors 2014, 14, 11957-11992.
2. Heo, J. S.; Kim, Y.-H.; Park, S. K. Recent Progress of Textile-Based Wearable Electronics: A Comprehensive Review of Materials, Devices, and Applications. Small 2017, 14 (3), 1703034.
3. Wang, X.; Liu, Z.; Zhang, T. Flexible Sensing Electronics for Wearable/Attachable. Small 2017, 13 (25), 1602790.
4. Bae, H.; Jang, B. C.; Park, H.; Jung, S.-H.; Lee, H. M.; Park, J.-Y.; Jeon, S.-B.; Son, G.; Tcho, I.-W.; Yu, K.; Im, S. G.; Choi, S.-Y.; Choi, Y.-K. Functional Circuitry on Commercial Fabric via Textile-Compatible Nanoscale Film Coating Process for Fibertronics. Nano Letters 2017, 17 (10), 6443-6452.
5. Yu, A.; Pu, X.; Wen, R.; Liu, M.; Zhou, T.; Zhang, K.; Zhang, Y.; Zhai, J.; Hu, W.; Wang, Z. L. Core-Shell-Yarn-Based Triboelectric Nanogenerator Textiles as Power Cloths. ACS Nano 2017, 11, 12764-12771.
6. Di, J.; Zhang, X.; Yong, Z.; Zhang, Y.; Li, D.; Li, R.; Li, Q. Carbon-Nanotube Fibers for Wearable Devices and Smart Textiles. Advanced Materials 2016, 28, 10529-10538.
7. Jost, K.; Stenger, D.; Perez, C. R.; McDonough, J. K.; Lian, K.; Gogotsi, Y.; Dion, G. Knitted and screen printed carbon-fiber supercapacitors for applications in wearable electronics. Energy & Environmental Science 2013, 6, 2698-2705.
8. Cherenack, K.; Zysset, C.; Kinkeldei, T.; Münzenrieder, N.; Tröster, G. Woven Electronic Fibers with Sensing and Display Functions for Smart Textiles. Advanced Materials 2010, 22 (45), 5178-5182.
9. Huang, Y.; Hu, H.; Huang, Y.; Zhu, M.; Meng, W.; Liu, C.; Pei, Z.; Ha, C.; Wang, Z.; Zhi, C. From Industrially Weavable and Knittable Highly Conductive Yarns to Large Wearable Energy Storage Textiles. ACS Nano 2015, 9 (5), 4766-4775.
10. Jin, H.; Abu-Raya, Y. S.; Haick, H. Advanced Materials for Health Monitoring with Skin-Based. Advanced Healthcare Materials 2017, 6 (11), 1700024.
11. Maccioni, M.; Orgiu, E.; Cosseddu, P.; Locci, S.; Bonfiglio, A. Towards the textile transistor: Assembly and characterization of an organic field effect transistor with a cylindrical geometry. Applied Physics Letters 2006, 89, 143515.
12. Yoon, S. S.; Lee, K. E.; Cha, H.-J.; Seong, D. G.; Um, M.-K.; Byun, J.-H.; Oh, Y.; Oh, J. H.; Lee, W.; Lee, J. U. Highly Conductive Graphene/Ag Hybrid Fibers for Flexible Fiber-Type Transistors. Scientific Reports 2015, 5, 16366.
13. Rossi, D. D. Electronic Textiles: A Logical Step. Nature Materials 2007, 6, 329.
14. Hamedi, M.; Forchheimer, R.; Inganäs, O. Towards woven logic from organic electronic fibres. Nature Materials 2007, 6, 357-362.
15. Xie, J.; Long, H.; Miao, M. High sensitivity knitted fabric strain sensors. Smart Materials and Structures 2016, 25, 105008.
16. Ryu, S.; Lee, P.; Chou, J. B.; Xu, R.; Zhao, R.; Hart, A. J.; Kim, S.-G. Extremely Elastic Wearable Carbon Nanotube Fiber Strain Sensor for Monitoring of Human Motion. ACS Nano 2015, 9 (6), 5929-5936.
17. Wu, X.; Han, Y.; Zhang, X.; Lu, C. Highly Sensitive, Stretchable, and Wash-Durable Strain Sensor Based on Ultrathin Conductive Layer@Polyurethane Yarn for Tiny Motion Monitoring. ACS Applied Materials & Interfaces 2016, 8 (15), 9936-9945.
18. Wang, C.; Li, X.; Gao, E.; Jian, M.; Xia, K.; Wang, Q.; Xu, Z.; Ren, T.; Zhang, Y. Carbonized Silk Fabric for Ultrastretchable, Highly Sensitive, and Wearable Strain Sensors. Advanced Materials 2016, 28 (31), 6640-6648.
19. Zysset, C.; Nasseri, N.; Büthe, L.; Münzenrieder, N.; Kinkeldei. Textile Integrated Sensors and Actuators for near-Infrared Spectroscopy. Optics Express 2013, 21, 3213-3224.
20. Yang, Y.-L.; Chuang, M.-C.; Lou, S.-L.; Wang, J. Thick-Film Textile-Based Amperometric Sensors and Biosensors. Analyst 2010, 135, 1230-1234.
21. Kim, K. N.; Chun, J.; Kim, J. W.; Lee, K. Y.; Park, J.; Kim, S.; Wang, Z. L. Highly Stretchable 2D Fabrics for Wearable Triboelectric Nanogenerator under Harsh Environments. ACS Nano 2015, 9 (6), 6394-6400.
22. Zhang, Z.; Chen, Y.; Debeli, D. K.; Guo, J. S. Facile Method and Novel Dielectric Material Using a Nanoparticle-Doped Thermoplastic Elastomer Composite Fabric for Triboelectric Nanogenerator Applications. ACS Applied Materials & Interfaces 2018.
23. Zeng, W.; Tao, X.-M.; Chen, S.; Shang, S.; Chan, H. L. W.; Choy, S. H. Highly durable all-fiber nanogenerator for mechanical energy harvesting. Energy & Environmental Science 2013, 6, 2631-2638.
24. Seung, W.; Gupta, M. K.; Lee, K. Y.; Shin, K.-S.; Lee, J.-H.; Kim, T. Y.; Kim, S.; Lin, J.; Kim, J. H.; Kim, S.-W. Nanopatterned Textile-Based Wearable Triboelectric Nanogenerator. ACS Nano 2015, 9 (4), 3501-3509.
25. Zhong, J.; Zhang, Y.; Zhong, Q.; Hu, Q.; Hu, B.; Wang, Z. L.; Zhou, J. Fiber-Based Generator for Wearable Electronics and Mobile Medication. ACS Nano 2014, 8 (6), 6273-6280.
26. Le, V. T.; Kim, H.; Ghosh, A.; Kim, J.; Chang, J.; Vu, Q. A.; Pham, D. T.; Lee, J.-H.; Kim, S.-W.; Lee, Y. H. Coaxial Fiber Supercapacitor Using All-Carbon Material Electrodes. ACS Nano 2013, 7 (7), 5940-5947.
27. Meng, Q.; Wang, K.; Guo, W.; Fang, J.; Wei, Z.; She, X. Thread-like Supercapacitors Based on One-Step Spun Nanocomposite Yarns. Small 2014, 10 (15), 3187-3193.
28. Yoon, J.; Jeong, Y.; Kim, H.; Yoo, S.; Jung, H. S.; Kim, Y.; Hwang, Y.; Hyun, Y.; Hong, W.-K.; Lee, B. H.; Choa, S.-H.; Ko, H. C. Robust and stretchable indium gallium zinc oxide-based electronic textiles formed by cilia-assisted transfer printing. Nature Communications 2016, 7, 11477.
29. Harnett, C. K.; Zhao, H.; Shepherd, R. F. Stretchable Optical Fibers: Threads for Strain-Sensitive. Advanced Materials Technologies 2017, 2 (9), 1700087.
30. Kim, D.-H.; Lu, N.; Ma, R.; Kim, Y.-S.; Kim, R.-H.; Wang, S.; Wu, J.; Won, S. M.; Tao, H.; Islam, A.; Yu, K. J.; Kim, T.-I.; Chowdhury, R.; Ying, M.; Xu, L.; Li, M.; Chung, H.-J.; Keum, H.; McCormick, M.; Liu, P.; Zhang, Y.-W.; Omenetto, F. G.; Huang, Y.; Coleman, T.; Roger, J. A. Epidermal Electronics. Science 2011, 333, 838.
31. Chung, H.; Sulkin, M. S.; Kim, J.; Goudeseune, C.; Chao, H.; Song, J. W.; Yang, S. Y.; Hsu, Y.; Ghaffari, R.; Efimov, I. R.; Rogers, J. A. Stretchable, Multiplexed pH Sensors With Demonstrations on Rabbit and Human Hearts Undergoing Ischemia. Advanced Healthcare Materials 2014, 3 (1), 59-68.
32. Gao, W.; Emaminejad, S.; Nyein, H. Y. Y.; Challa, S.; Chen, K.; Peck, A.; Fahad, H. M.; Ota, H.; Shiraki, H.; Kiriya, D.; Lien, D.-H.; Brooks, G. A.; Davis, R. W.; Javey, A. Fully integrated wearable sensor arrays for multiplexed in situ perspiration analysis. Nature 2016, 529, 509.
33. Yokota, T.; Inoue, Y.; Terakawa, Y.; Reeder, J.; Kaltenbrunner, M.; Ware, T.; Yang, K.; Mabuchi, K.; Murakawa, T.; Sekino, M.; Voit, W.; Sekitani, T.; Someya, T. Ultraflexible, large-area, physiological temperature sensors for multipoint measurements. Proc. Natl. Acad. Sci. USA 2015, 112, 14533.
34. Drack, M.; Graz, I.; Sekitani, T.; Someya, T.; Kaltenbrunner, M.; Bauer, S. An imperceptible plastic electronic wrap. Advanced Materials 2015, 27 (1), 34-40.
35. Lipomi, D. J.; Vosgueritchian, M.; Tee, B. C.-K.; Hellstrom, S. L.; Lee, J. A.; Fox, C. H.; Bao, Z. Skin-like pressure and strain sensors based on transparent elastic films of carbon nanotubes. Nature Nanotechnology 2011, 6, 788-792.
36. Kim, B.-S.; Lee, S. W.; Yoon, H.; Strano, M. S.; Shao-Horn, Y.; Hammond, P. T. Pattern Transfer Printing of Multiwalled Carbon Nanotube Multilayers and Application in Biosensors. Chemistry of Materials 2010, 22 (16), 4791-4797.
37. Cottet, D.; Grzyb, J.; Kirstein, T.; Tröster, G. Electrical characterization of textile transmission lines. IEEE Trans. Adv. Packag. 2003, 26, 182-190.
38. Bhat, N. V.; Seshadri, D. T.; Radhakrishnan, S. Preparation, Characterization, and Performance of Conductive Fabrics: Cotton+PANi. Textile Research Journal 2004, 74 (2), 155-166.
39. Matsuhisa, N.; Kaltenbrunner, M.; Yokota, T.; Jinno, H.; Kuribara, K.; Sekitani, T.; Someya, T. Printable elastic conductors with a high conductivity for electronic textile applications. Nature Communications 2015, 6, 7461.
40. Jin, H.; Matsuhisa, N.; Lee, S.; Abbas, M.; Yokota, T.; Someya, T. Enhancing the Performance of Stretchable Conductors for E-Textiles by Controlled Ink Permeation. Advanced Materials 2017, 29, 1605848.
41. Richards, H. R. Thermal Degradation of Fabrics and Yarns—Part I: Fabrics. Journal of the Textile Institute 1984, 75 (1), 28-36.
42. SNS NANOFIBER TECHNOLOGY, LLC, 2018. www.snsnano.com/pdf/PR-014%20NANOSAN-Sorb%20Technical%20Data%20Sheet.pdf (accessed Mar. 29, 2018).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An electronic textile apparatus comprising:
   a) a porous textile having fibers, a surface, and an opposite surface;
   b) a patterned electrically conductive wire that coats a portion of the fibers at the surface of the textile;
   c) an electrode that coats a portion of the fibers at the opposite surface of the textile; and
   d) an electrically conductive interconnect that coats a portion of the fibers within the textile, disposed between the surface and the opposite surface of the textile, and in contact with the wire and the electrode; wherein the wire, the electrode and the interconnect comprise an elastomer and metal particles.

2. The apparatus of claim 1 wherein the fibers are synthetic fibers such as a fiber comprising electrospun polyurethane.

3. The apparatus of claim 1 wherein the textile has a pore size of about 1 micron to about 100 microns.

4. The apparatus of claim 1 wherein the surface and the opposite surface of the textile has coated fibers up to a depth of about 100 microns within the textile.

5. The apparatus of claim 1 wherein the elastomer is a fluoropolymer or a fluorocopolymer.

6. The apparatus of claim 1 wherein the metal particles have a diameter of up to about 10 microns.

7. The apparatus of claim 1 wherein the textile has an electrical resistance ratio of about 10 or less than 10 after about 1000 cyclic stretches from zero to about 30% strain at a rate of about 4% strain per second.

8. An electronic textile apparatus comprising:
a) a porous textile having fibers, a surface, and an opposite surface;
b) a patterned electrically conductive pad that coats a portion of the fibers at the surface of the textile;
c) a conductive pad that has two-layer structure, where the top layer comprises conductive material and the bottom layer shows a joined fibrous structure wherein the fibers of the textile are amalgamated by a polymeric additive;
wherein the wire, the electrode and the interconnect comprise an elastomer and metal particles.

9. The apparatus of claim 8 wherein the fibers are synthetic fibers such as a fiber comprising electrospun polyurethane.

10. The apparatus of claim 8 wherein the two-layer structure is prepared by squeezing synthetic fibers in the presence of printed conductive ink material, wherein the conductive ink material comprises about 1 part to about 5 parts of (a) a fluorocopolymer, about 1 part to about 5 parts of (b) an organic solvent, and about 1 part to about 5 parts of (c) metal flakes.

11. The apparatus of claim 8 wherein the elastomer is a fluoropolymer or a fluorocopolymer.

12. The apparatus of claim 8 wherein the metal particles have a diameter of up to about 10 microns.

13. The apparatus of claim 8 wherein the textile has an electrical resistance ratio of about 10 or less than 10 after about 1000 cyclic stretches from zero to about 30% strain at a rate of about 4% strain per second.

14. An ink composition comprising about 1 part to about 5 parts of (a) a fluorocopolymer, about 1 part to about 5 parts of (b) an organic solvent, and about 1 part to about 5 parts of (c) metal flakes.

15. The composition of claim 14 wherein the composition has a ratio of (a):(b):(c) of about 4:3:3.

16. The composition of claim 14 wherein the metal flakes are silver flakes having a diameter of about 1 micron to about 10 microns.

17. The composition of claim 14, wherein the size of the metal flakes can be controlled to adjust the level of ink permeation.

18. The composition of claim 14 wherein the organic solvent is a ketone.

19. A method for fabricating a stretchable electronic textile from the composition of claim 14 comprising:
a) printing a circuit with the ink composition of claim 14 on a porous textile having fibers;
wherein a wire is printed on a surface of the textile, and an electrode is printed on the opposite surface of the textile;
b) inserting the composition of claim 14 into the textile to provide an electrical contact between the wire and the electrode, thereby forming a completed circuit;
c) drying the completed circuit;
wherein the printable ink coats a portion of the fibers that forms the completed circuit, and the textile has an electrical resistance ratio of about 10 or less than 10 after about 1000 cyclic stretches from zero to about 30% strain at a rate of about 4% strain per second.

20. The method of claim 19 wherein the fibers are synthetic fibers such as a fiber comprising electrospun polyurethane and the textile has a pore size of about 1 micron to about 100 microns.

21. The method of claim 19 wherein the completed circuit comprises a circuit for a wearable medical device.

22. The method of claim 19 wherein the completed circuit comprises a circuit for surface electromyography.

23. The method of claim 19 wherein the completed circuit is configured to sense at least one of electromyography (EMG), electroencephalography (EEG), electrocardiography (ECG), electrooculography (EOG), respiratory rate, heart rate, mechanical strain, pressure, temperature, vibration, and combinations thereof.

24. The method of claim 19 wherein the completed circuit is configured to provide stimulus of at least one type from the group consisting of visual, audio, mechanical, electrical, temperature, and combinations thereof.

* * * * *